(12) United States Patent
Agnew

(10) Patent No.: US 10,685,646 B2
(45) Date of Patent: Jun. 16, 2020

(54) VOICE CONTROL OF A FLOTATION TANK

(71) Applicant: Orbit Float Ltd, Hertfordshire (GB)

(72) Inventor: Robert Mackean Agnew, Hertfordshire (GB)

(73) Assignee: Orbit Float Ltd, Herfordshire (GB)

( * ) Notice: Subject to any disclaimer, the term of this patent is extended or adjusted under 35 U.S.C. 154(b) by 182 days.

(21) Appl. No.: 15/680,941

(22) Filed: Aug. 18, 2017

(65) Prior Publication Data
US 2018/0053508 A1 Feb. 22, 2018

Related U.S. Application Data

(60) Provisional application No. 62/376,456, filed on Aug. 18, 2016.

(51) Int. Cl.
*G10L 15/22* (2006.01)
*G10L 25/84* (2013.01)
(Continued)

(52) U.S. Cl.
CPC .......... *G10L 15/22* (2013.01); *A61H 33/6005* (2013.01); *A61M 21/0094* (2013.01); *A61M 21/02* (2013.01); *G10L 25/51* (2013.01); *G10L 25/84* (2013.01); *A61H 2033/0037* (2013.01); *A61H 2201/501* (2013.01);
(Continued)

(58) Field of Classification Search
CPC ........ A61H 33/6005; A61H 2201/5058; A61H 2033/0037; A61H 2201/5048; A61H 2201/5064; A61H 2201/5092; A61H 2201/501; A61M 2021/0027; A61M 21/0094; A61M 21/02; A61M 2021/0016; A61M 2021/0022; A61M 2021/005; A61M 2021/0066; A61M 2205/053; A61M 2205/332; A61M 2205/3375; A61M 2205/80; A61M 2230/63; G10L 15/22;
(Continued)

(56) References Cited

U.S. PATENT DOCUMENTS

2014/0012068 A1 1/2014 Hoefler
2014/0179859 A1 6/2014 Chen et al.
(Continued)

FOREIGN PATENT DOCUMENTS

CN 2582591 Y 10/2003
DE 10063807 A1 7/2002
(Continued)

OTHER PUBLICATIONS

"Floataway—Products/Technical Advancements", retrieved from http://web.archive.org/web/20151029062105/http://www.floataway.com/index.php/products/technical-advancements; as early as Oct. 2015.
(Continued)

*Primary Examiner* — Christine H Matthews
*Assistant Examiner* — Joshua Daryl D Lannu
(74) *Attorney, Agent, or Firm* — Brown & Michaels, PC

(57) ABSTRACT

By combining efficient manufacturing technology, design for user-centric comfort and accessibility with advanced automated operator control and operational features, the float tank methods and systems described herein provide clients with a personalized float experience, voice and non-tactile control interfacing, and float facility owners with highly profitable and reliable equipment.

19 Claims, 24 Drawing Sheets

(51) Int. Cl.
*G10L 25/51* (2013.01)
*A61H 33/00* (2006.01)
*A61M 21/00* (2006.01)
*A61M 21/02* (2006.01)
*C02F 1/32* (2006.01)
*C02F 103/42* (2006.01)
*C02F 1/00* (2006.01)

(52) U.S. Cl.
CPC ............. *A61H 2201/5048* (2013.01); *A61H 2201/5058* (2013.01); *A61H 2201/5064* (2013.01); *A61H 2201/5092* (2013.01); *A61M 2021/005* (2013.01); *A61M 2021/0016* (2013.01); *A61M 2021/0022* (2013.01); *A61M 2021/0027* (2013.01); *A61M 2021/0066* (2013.01); *A61M 2205/053* (2013.01); *A61M 2205/332* (2013.01); *A61M 2205/3375* (2013.01); *A61M 2205/80* (2013.01); *A61M 2230/63* (2013.01); *C02F 1/001* (2013.01); *C02F 1/32* (2013.01); *C02F 2103/42* (2013.01); *G10L 2015/223* (2013.01)

(58) Field of Classification Search
CPC ... G10L 25/51; G10L 25/84; G10L 2015/223; C02F 1/001; C02F 2103/42; C02F 1/32
See application file for complete search history.

(56) References Cited

U.S. PATENT DOCUMENTS

2015/0141741 A1  5/2015  Sullivan
2015/0306341 A1* 10/2015  Hoefler ............. A61M 21/0094
                                                        600/21
2015/0346810 A1* 12/2015  Urbach ................... G06F 3/011
                                                        345/156

FOREIGN PATENT DOCUMENTS

EP       0666049 A1    8/1995
EP       1639985 A1    3/2006
EP       1688122 A1    8/2006

OTHER PUBLICATIONS

Kommineni et al., "3.0 Advanced Oxidation Processes", published by the United States National Water Research Institute; Dec. 2008.
Search Report for GB1614190.5 dated Jan. 27, 2017.

* cited by examiner

DOOR MOSLY CLOSED

FIG. 13 Details of door mechanism

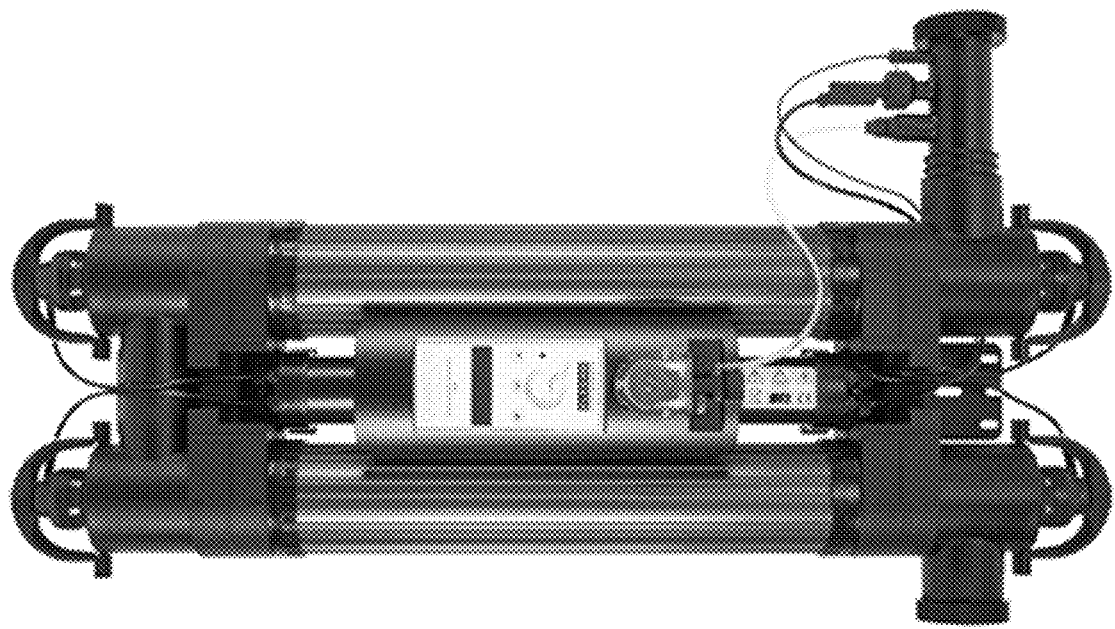
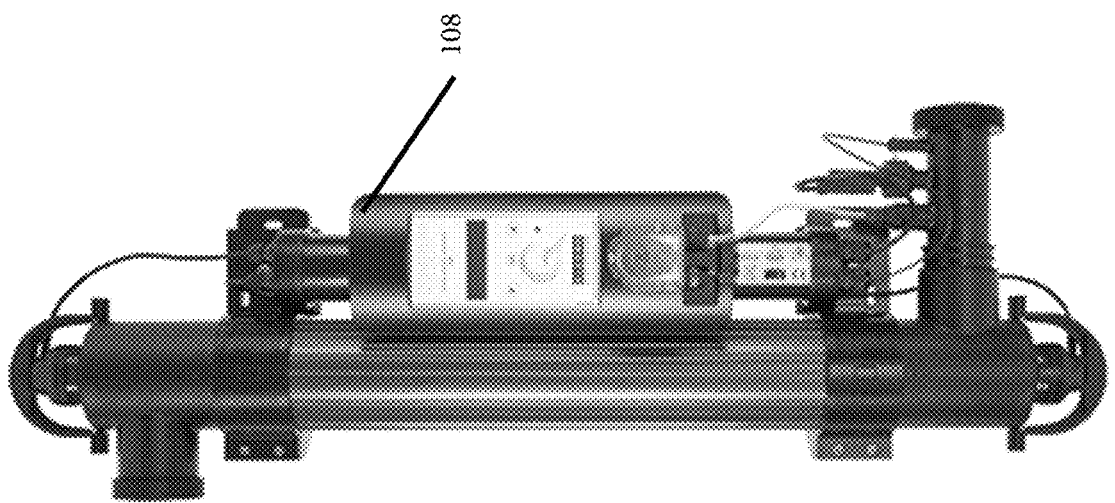
FIG. 15

Details of photocatalytic hybrid UV hydroxyl oxidizer

VOICE CONTROL OF A FLOTATION TANK

CROSS-REFERENCE TO RELATED APPLICATIONS

This application claims one or more inventions which were disclosed in Provisional Application No. 62/376,456 filed Aug. 18, 2016, entitled "FLOATATION TANK". The benefit under 35 USC § 119(e) of the U.S. provisional application is hereby claimed, and the aforementioned application is hereby incorporated herein by reference.

BACKGROUND

The invention pertains to the field of non-tactile sensory deprivation flotation control systems and methods. More particularly, the invention pertains to voice control of a sensory deprivation float tank system.

SUMMARY

A sensory deprivation float tank system may include a tank that has a multi-segment shell comprising an outer surface, an inner surface substantially surrounding a sensory deprivation flotation space and a housing wall disposed between the outer surface and the inner surface, and an opening providing human access into the flotation space. The tank may also include a movable panel shaped to cover the opening by moving from an open position to a closed position, wherein the movable panel forms a light and sound barrier for the sensory deprivation flotation space when it is disposed in the closed position. The tank may further include a bottom portion of the inner surface comprising a plurality of apertures at least a portion of which are for at least one of filling a portion of the flotation space with solution, emptying the solution from the flotation space and delivering a gas to the flotation space. To provide user access the tank may also include a plurality of handles disposed on the inner surface. Additionally, the tank includes a plurality of ports disposed in a lower region of the inner surface through which a solution flows into the flotation space, the lower region proximal to the bottom portion. The tank system may also include a solution purification unit disposed to perform at least one of receive solution from the flotation space and deliver solution to the flotation space, wherein the solution purification unit filters at least 99.99 of particles 0.1 microns in diameter or larger. A solution storage tank may also be operatively coupled to the shell, wherein solution flowing between the shell and the tank are processed with the solution purification unit.

The float tank system may further include a solution storage tank and a solution purification unit that are connected to facilitate, during storage mode, processing of the solution in the storage tank with the solution purification unit. During emptying, the solution flows from the flotation space through the purification unit to the tank.

In the float tank system, the solution purification unit comprises a hydroxyl radical technology-based dual pass ultraviolet filtering portion. Solution passing through the solution purification unit is exposed to hydroxyl radical technology-based ultraviolet light. Optionally, the float tank system may include a mechanical filter that retains at least 99.999% of bacteria that is present in the solution that passes through the mechanical filter. Optionally the float tank system may alternatively include a carbon filter disposed in place of the mechanical filter through which the solution flows.

The float tank design may contribute to the inner surface including a plurality of curved surfaces and a single planar surface. The single planar surface may be the bottom portion. Optionally, the inner surface comprises all curved surfaces other than the bottom portion.

In the float tank system, a portion of the interior disposed between the outer surface and the bottom portion of the inner surface comprises heating panels disposed to heat up the bottom portion of the inner surface when activated.

A float tank system may include a plurality of sensors disposed to monitor at least one aspect of each of the solution in the flotation space, air disposed in the flotation space above the solution, audio produced within the tank, movement by a user within the tank, movement of the fluid within the tank, and biometric parameters of a user disposed in the flotation space.

The float tank may be constructed so that the inner surface comprises a hydrophobic material, or is coated with hydrophobic material.

To enhance user comfort, the float tank system may further include a mist-spray source disposed in the flotation space so that a mist-spray emanating from the source is directed at a face of a user floating face-up in the solution. Additionally, a towel may be attached to a first end of an elasticized cord, the elastic cord being anchored by a second end of the elastic cord to a non-movable portion of the shell, wherein in an unexpanded (neutral) mode, the towel remains suspended above the solution.

Control of lighting for the float tank may include a method of visually signaling a pending start and a pending end of a flotation session of a user disposed in a flotation space of a flotation tank. A pending start may be indicated by generating, during a flotation start time interval, a first light pattern by controlling a plurality of illumination sources disposed to illuminate the flotation space, the first pattern emulating a sunset. A pending end may be indicated by generating, during a flotation end time interval, a second light pattern by controlling the plurality of illumination sources disposed to illuminate the flotation space, the second pattern emulating a sunrise.

These and other systems, methods, objects, features, and advantages of the present disclosure will be apparent to those skilled in the art from the following detailed description of the preferred embodiment and the drawings.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

BRIEF DESCRIPTION OF THE DRAWINGS

FIG. 15 depicts end and side views of an embodiment of an ultraviolet filtration sub-system.

DETAILED DESCRIPTION

Figure 1:
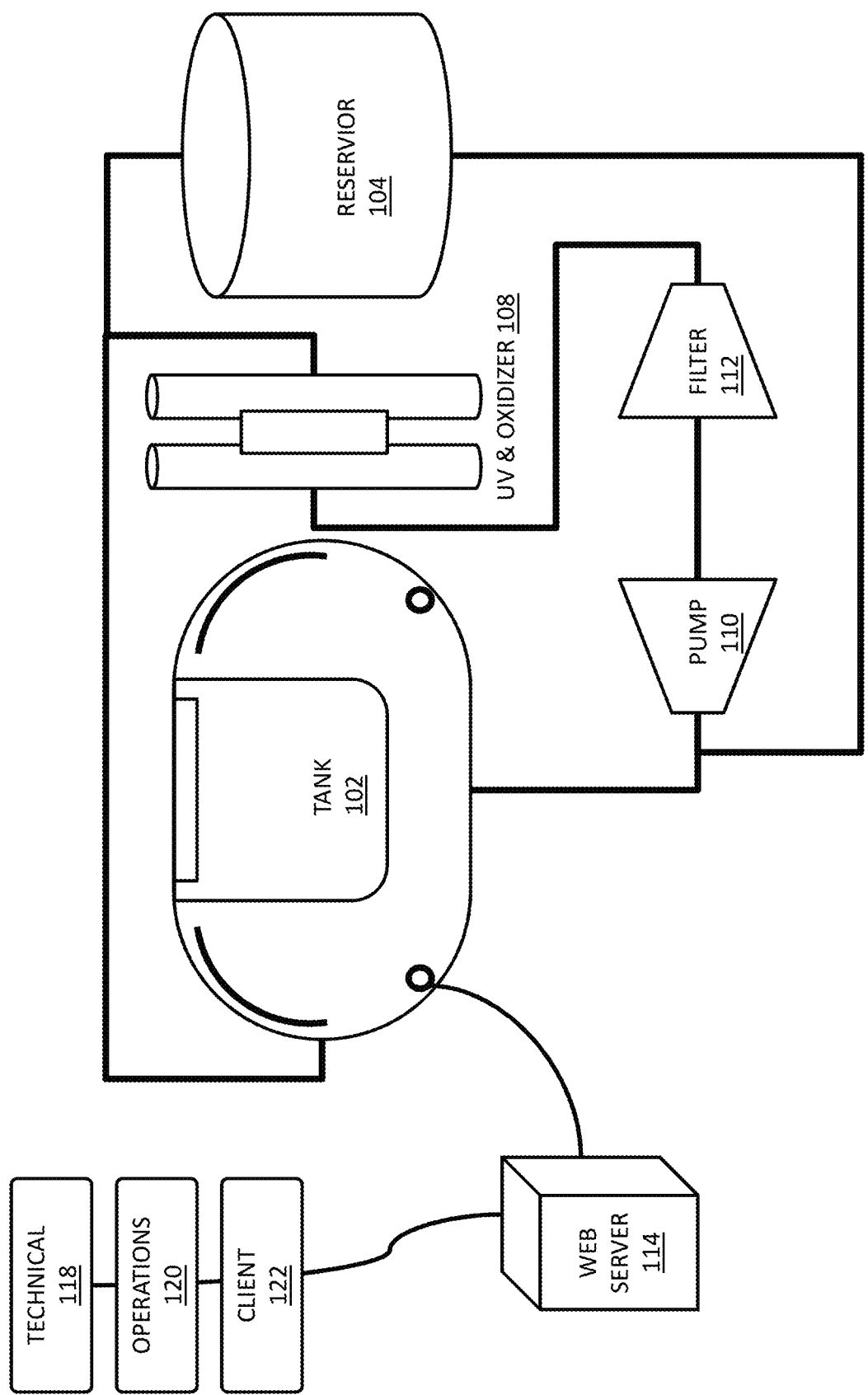
FIG. 1 depicts a schematic diagram of a sensory deprivation float tank system.

A float tank system as depicted in FIG. 1, may include a covered tank 102 with a top-opening door that slides from a closed position to an open position so that a user can be upright in the float tank while standing in the opening made by the opened door. The float tank system may include a plurality of float fluid flow and quality control elements to ensure high quality float fluid is processed between float tank uses. The float fluid control elements may include a plurality of segments of pipe operably attached to the tank 102 while being disposed outside of the tank connecting other float fluid elements including at least one float fluid pump 110 for moving the float fluid throughout the system. The float fluid pump 110 may direct fluid from the tank 102 through a one or more filtration systems 112 and 108 to a float fluid reservoir 104. The float fluid pump 110 may also direct fluid from the float fluid reservoir 104 to the tank 102, optionally directing the float fluid through at least a portion of the plurality of filtration systems 112 and 108. The float fluid pump 110 may also direct fluid from the fluid reservoir 104, through the one or more filtration systems 112 and 108, and back to the fluid reservoir 104. The float tank system depicted in FIG. 1 may further include float tank system control elements, such as a computer that may be a web server 114, one or more remote devices that may include one or more user interfaces including a client user interface 122, an operations user interface 120 and a technical user interface 118.

The float tank system may include a float tank 102 as depicted variously in the figures of the present application. Various exemplary embodiments of a float tank of the present invention may be found in FIGS. 5-12.

The float tank system may also include computer networking capabilities, such as wireless networking for communicating with controllable hardware elements disposed inside, within the wall of, and/or in close proximity too the tank. Controllable hardware elements may include motorized door opener/closer, interior door-mounted display screen, float fluid monitoring sensors, tank air monitoring sensors, aromatherapy management systems, interior and/or exterior float tank lighting, float fluid pump, user control panel(s), operator control panels, audio systems, video systems, emergency stop/start user interface, one or more float fluid filtration subsystems, and the like. The one or more float fluid filtration subsystems may include at least one of a charcoal filter, a sub-micron filter, micron (e.g., bag) filter, dual pass hybrid photocatalytic UV hydroxyl radical oxidizer, float fluid pump, float fluid routing valves, and the like.

The float tank system may further include a plurality of types of user interfaces for electronic devices including laptop computers, tablets, mobile phones, display watches, stationary display screens, and the like. The user interfaces may be compatible with conventional web browsers, allowing any user with an electronic device and a conventional browser to access and operate the user interface. User interface types may include a technical user interface, an operations user interface, a client user interface, and the like.

A technical user interface of the float tank system may include display and/or control of fluid and air temperature, fluid pH level, hydrogen peroxide level, chlorine level, fluid density, filter life indicator/estimated time for filter change, solution level, ultraviolet filter bulb life, pump operational time and/or flow, heater usage, power consumption of a plurality of electronically powered elements of the float tank system, actual, projected, and estimated running costs, and the like.

An operations user interface of the float tank system may include float session time-related information (time to next client, time since float started, remaining float time for an active float session), audio output (e.g., music) selection, volume and the like, lighting mode, float tank operational status (e.g., client in/out of tank, client standing, client floating, client vital biologic signs, door open/closed, auto start status, and the like.

A client user interface of the float tank system may include a client-specific message that may include a welcome message, the user's name, user profile settings, audio content access and control (e.g. user customized audio library, playlist, and the like), accessory and other services offers, float session booking, access to a directory of float tank center, promotions, user loyalty offers, and the like.

A float tank system may operate in a variety of modes including fill, float, empty, pre-clean, storage, and the like. A float tank system may perform a procedure to empty a float tank, filter the float fluid, store the float fluid in a reservoir, pump the fluid out of the reservoir and refill the float tank with approximately between 800 and 900 liters of float fluid in under 6 minutes using the methods and systems described herein.

Computer-based monitoring and control of a float tank system as described and depicted herein may include control of interior float tank lighting, exterior float tank lighting, float tank external ambient lighting and the like. Lighting may be controlled to meet individual user's preferences, requirements, and the like by allowing each user to customize the lighting control operations. Users may be offered a plurality of predefined lighting schemes that may include interior, exterior and/or ambient light control. A user may select a lighting scheme and save it as his/her preferred or default lighting scheme so that each time he/she attends a float session, this lighting scheme may be activated. Likewise, a user may override any default, predefined, or preferred lighting scheme by specifying or selecting an alternate lighting scheme. A lighting scheme may include various phases of a float session including, pre entry, standing entry, top closing, float start, floating, float ending, top opening, standing exit, post exit and the like. Interior lighting may be adjusted for each phase independently of exterior or external ambient lighting. A given lighting scheme may be used in any number of phases or each phase may have a different lighting scheme.

Computer-based monitoring and control of a float tank system as described and depicted herein may include temperature monitoring and control of float fluid, interior air, exterior air and the like. While various algorithms may be applied to handle changes in any of these temperature controlled mediums, generally the interior air and the float fluid are controlled to be essentially the same temperature. This is typically accomplished by maintaining the float fluid at a predefined temperature such as 97.5 F+/−2 F and adjusting the air temperature inside the float tank to closely match the float fluid temperature.

Computer monitoring, such as through the use of temperature sensors for the air and float fluid may provide automated control of heaters and/or coolers to adjust the air temperature. In addition to monitoring and controlling the temperature of the interior air of a float tank, a temperature of at least an inner shell of the float tank may also be controlled. Moisture build up (e.g., condensation) and potential dripping may be avoided by maintaining temperatures of the inner shell (e.g., interior surface) and interior air to be within a few degrees of one another.

Computer-based monitoring and control of a float tank system as described and depicted herein may include controlling sound within a float tank. In an embodiment, a sound transducer that converts an audio signal to vibrations that cause at least a portion of the float tank enclosure to produce sound similarly to an audio speaker may be employed. This may be produced by operationally connecting a speaker cone to a portion of the tank housing, such as the inner shell to facilitate vibrating the inner skin (e.g., inner shell) to produce musing. Alternatively, speakers may be embedded into the shell of the tank. In addition to producing sound in the interior of the float tank, external sounds may be kept from reaching the interior of the housing through use of noise insulating material in the housing, tight coupling of the door to the housing when the door is closed, active noise cancellation techniques and the like.

In regards to audio selection, a user may select one or more audio tracks (e.g., songs, melodies, and the like) to be played during his/her float session. Alternatively, a user interface may facilitate access by the user to various audio streaming services, such as PANDORA®, SPOTIFY®, and the like. Yet further, the user may specify particular songs from a library of songs to which a computer that controls the audio of the float tank has access. The float tank may include a physical or wireless port to which a user may connect an audio player, such as an audio player on a smart phone or the like. In an example, a user may use BLUETOOTH® audio to connect his/her digital audio player to the audio control system of the float tank through which the connected audio player can play audio.

A display monitor may be mounted on an interior surface, such as the interior of the sliding door. A user may, using an approach similar to audio and lighting control, determine the content that is presented on this monitor. Additionally, messages, such as information related to a float session may be presented to the user on such a monitor. The monitor may be protected from condensation of the float fluid to avoid corrosion through various techniques including insulation, vapor barriers, active condensation prevention and control, and the like.

Unlike hinged doors, the sliding door of the float tank may be configured to support any additional weight imposed by the monitor while ensuring smooth opening and closing. Automated, or assisted opening and closing mechanisms as described and depicted herein may compensate for the weight of such a monitor.

Computer monitoring and operation of a range of aspects of float tank operation, float sessions, and the like may facilitate compliance with standards for user safety, float quality, and the like. In-line and various placed sensors may facilitate computer monitoring of float fluid temperature, air temperature, float fluid quality, PH level, pressure and the like. In-line pressure sensors, particularly those disposed proximal to outlet ports of the tank, may be used to determine when a customer assumes the float position. When a person assumes the float position in the tank, there is an increase in pressure due the level of the salt solution increasing (e.g., Archimedes principle) and an in-line pressure transducer can measure this. This pressure can be monitored so that a float tank operations interface can automatically detect a start of a float session. Algorithms may process these and other sensed aspects, such as by comparing sensed values to threshold values. When a sensed value exceeds a threshold, an alert may be generated so that an operator may take corrective action. Alternatively, when a sensed value exceeds a threshold, an automated control process may be performed to take corrective action, such as increasing air temperature, infusing hydrogen peroxide and the like with an automated dispensing system. A plurality of thresholds for any monitored aspect. A computer receiving data from various monitors (e.g., PH, temperature, quality, and the like) may indicate a sensed value is approaching an actionable threshold, or is approaching a threshold for shutting down the float tank system until corrective action can be taken. In an example, a first threshold may result in an operator being alerted to verify that an automated dispensing system is operational; a second threshold may cause the automated dispensing system to activate; a third threshold may alert the operator to terminate the float session.

Computer monitoring and operation of a range of aspects of the float tank operation may include automated dosing systems, such as dosing pumps for hydrogen peroxide and the like. Such systems may be responsive to monitored aspects of the float tank including float fluid temperature, PH, quality and the like. Such systems may also be responsive to operator control, such as through an operational interface for computer controlling the dosing systems and the like.

Computer monitoring and operation of a range of aspects of the float tank system may be performed during any mode of the system including float operation, float fluid storage, float tank filling and/or emptying. A range of aspects of the float tank system may be monitored including temperature, pH, hydrogen peroxide levels, chlorine levels, solution level, salinity, condition of filter(s), ultraviolet light status, presence of a user, door open/closed, lights on/off, float session duration, fill time, empty time, and the like. Additionally, monitoring may include bio-sensors for the float tank user. Sensors may track a user's breathing, heart rate, movement, sleep state, and the like.

Figure 2:
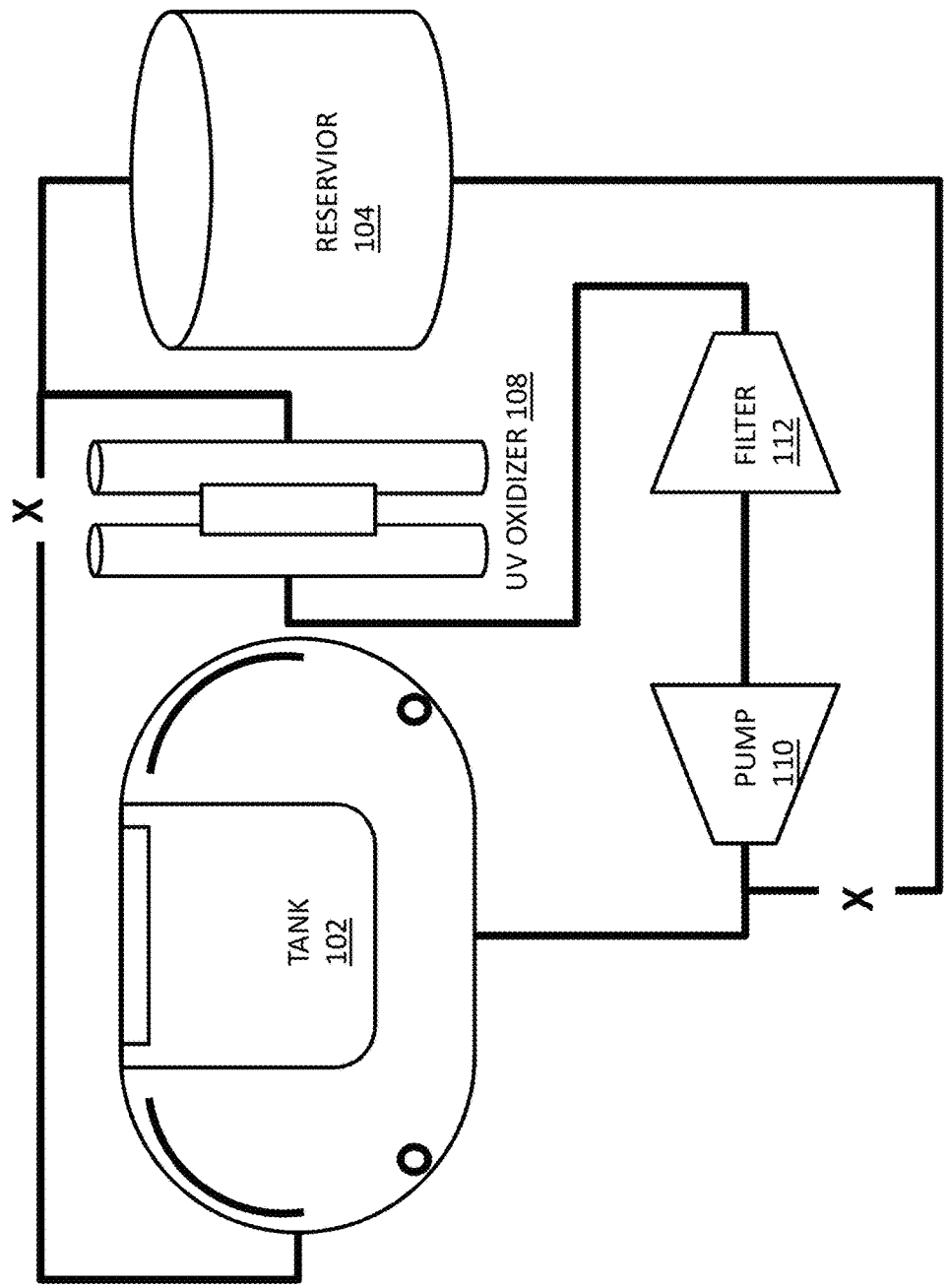
FIG. 2 depicts a schematic diagram of a float tank system during an emptying operation.

An empty operation may be depicted in FIG. 2. An empty operation may be performed (optionally automatically) after a float session. Float fluid is directed by the pump 110 from the tank 102 through the filter 112 and the UV oxidizer 108 to the reservoir 104, where it may be retained to reduce evaporation and retain temperature (e.g., mitigate heat loss). Computer control system 114 may monitor, such as through level sensors disposed inside the tank 102 and/or flow sensors disposed to sense fluid emptying out of the tank 102, and/or pump operational sensors, reservoir fill sensors, and the like, the fluid level, among other things, and control the pump 110 accordingly to achieve a predetermined degree of emptiness of the fluid from the tank 102.

Figure 3:
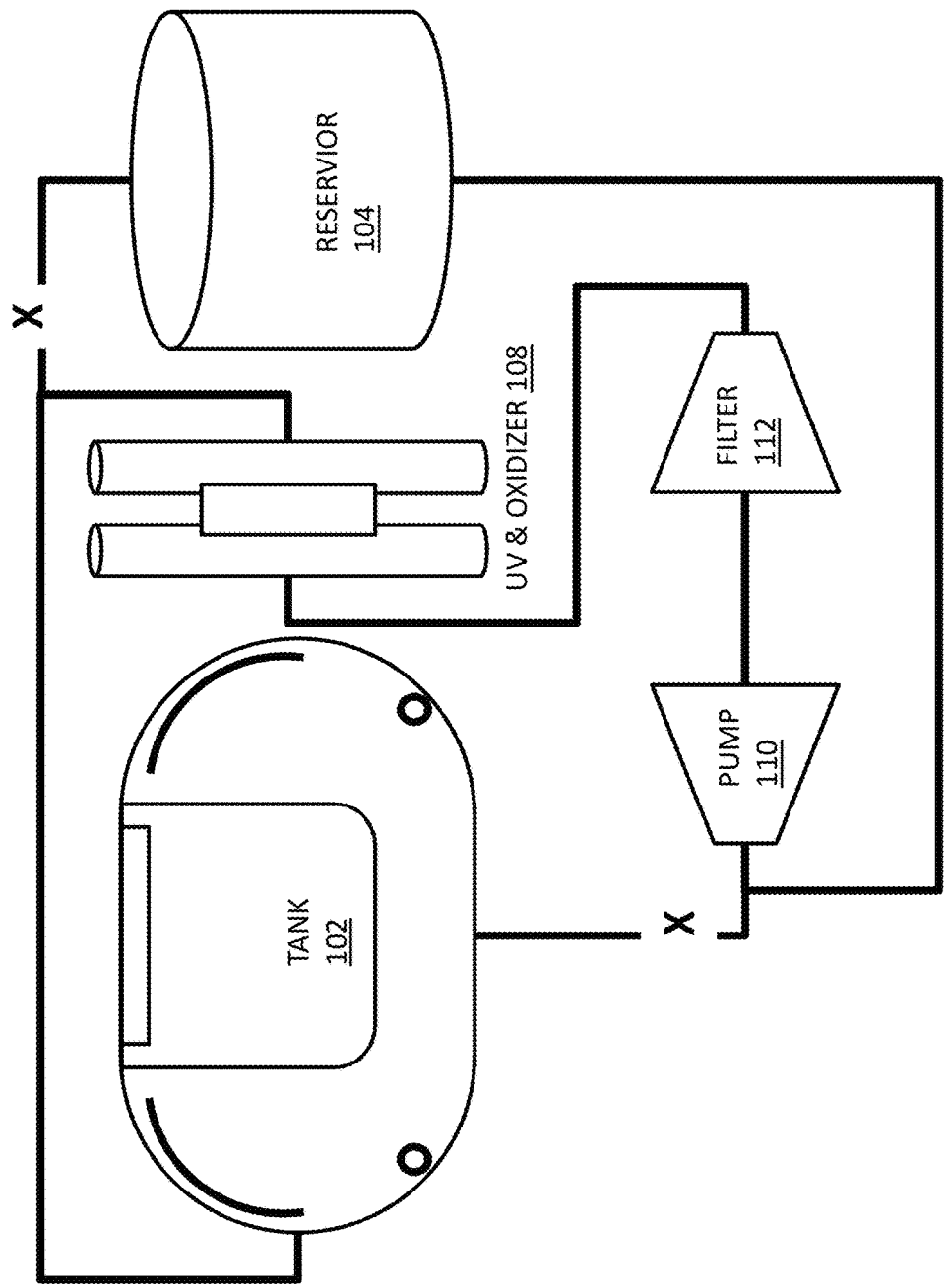
FIG. 3 depicts a schematic diagram of a float tank system during a filling operation.

A fill operation mode may be depicted in FIG. 3. Float fluid is directed by the pump 110 from the reservoir 104 to a filter 112 and through a UV oxidizer 108, ending up at an inlet port of the tank 102. Computer control system 114 may monitor, such as through level sensors disposed inside the tank 102 and/or flow sensors disposed to sense fluid filling the tank 102, and/or pump operational sensors, and the like the fluid level, among other things, and control the pump 110 accordingly to achieve a predetermined level of float fluid in the tank 102.

Figure 4:
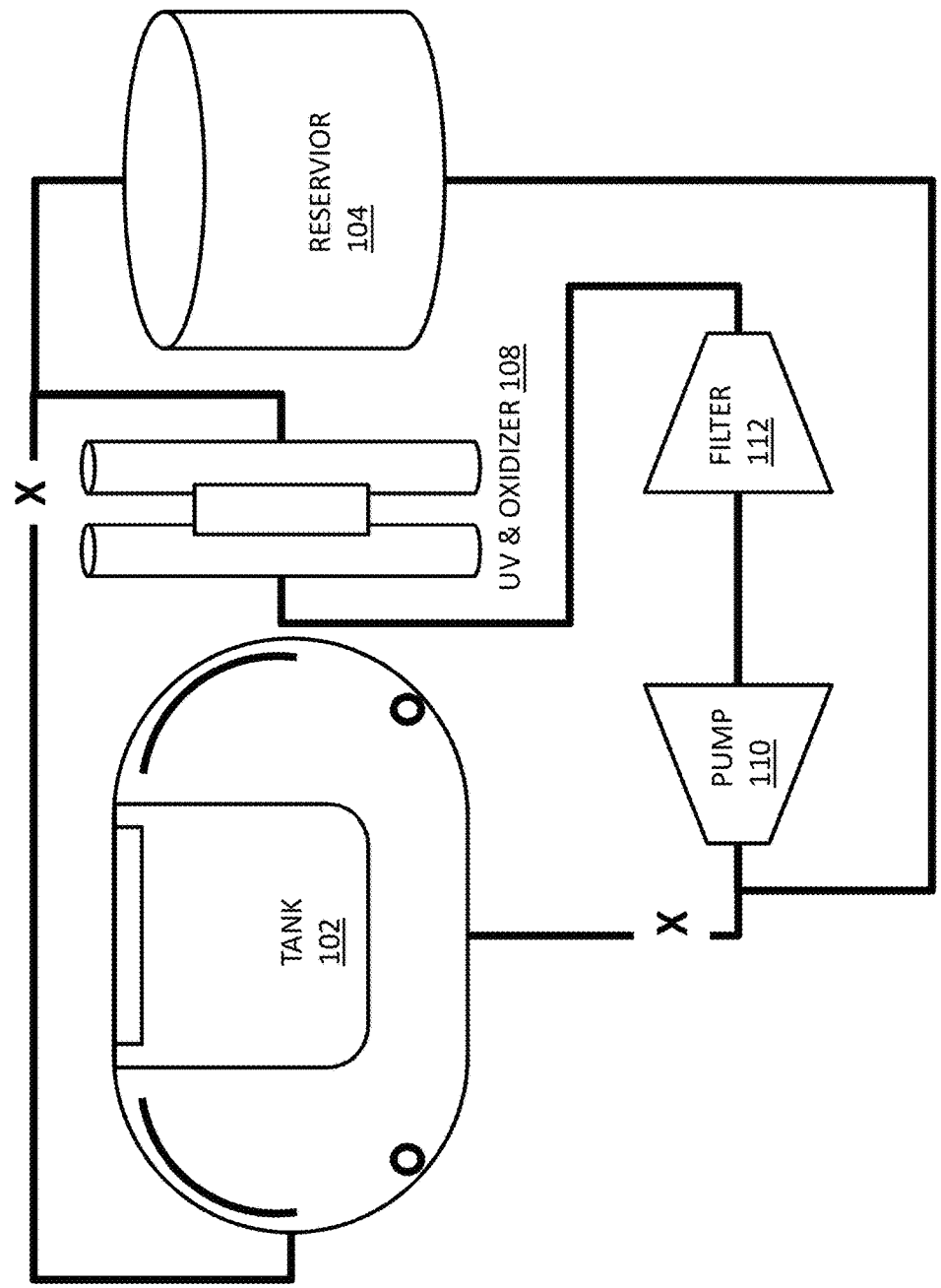
FIG. 4 depicts a schematic diagram of a float tank system during a storage filtering operation.

A storage filtering operation mode may be depicted in FIG. 4. Storage filtering may preferably occur on a scheduled basis and/or based on sensed float fluid characteristics, such as contaminant level, float fluid temperature, and the like. During times of storage in the reservoir that exceeds a float fluid filter time threshold, float fluid may be directed by the pump 110 from the reservoir 104 to filter 112 and through UV oxidizer 108, ending up at the inlet port of the reservoir tank 104. Computer control system 114 may monitor, such as through level sensors disposed inside the tank 102 and/or flow sensors disposed to sense fluid filling the tank 102, and/or pump operational sensors, and the like the fluid level, among other things, and control the pump 110 accordingly to achieve a predetermined level of float fluid in the tank 102.

Figure 5:
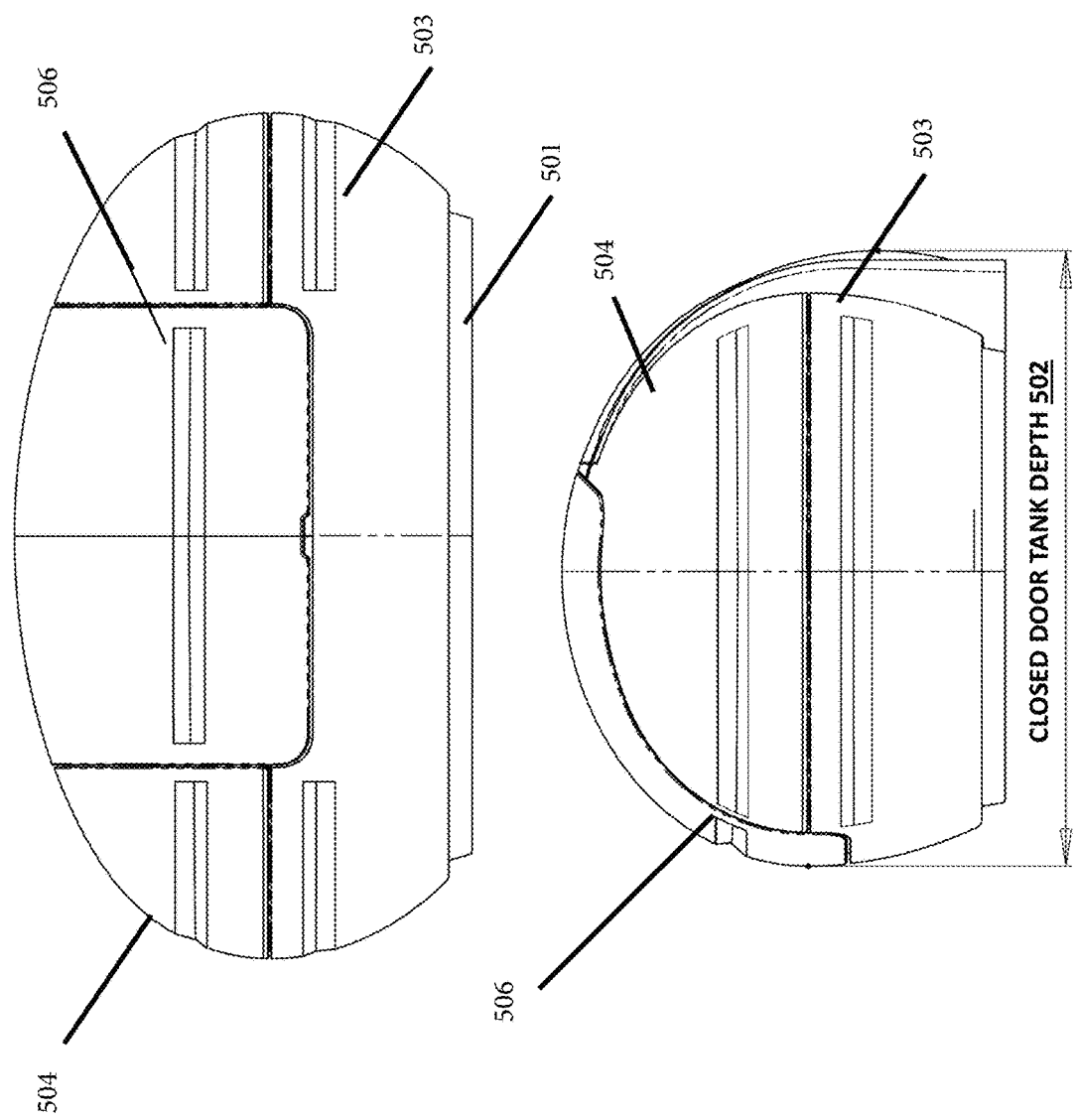
FIG. 5 depicts exterior side and end views of the float tank.

FIG. 5 depicts exterior side and end views of the float tank with the door closed, as would be the case when a float session is in progress. The float tank of FIG. 5 has a substantially oval shape, with a bottom portion 501 adapted for placement of a flat surface such as a floor or other sturdy surface. The float tank of FIG. 5 may include a lower body portion 503, an upper body portion 504 that attaches to the lower body portion 503, and a door assembly that attaches to the lower body portion 503 and may optionally attach at least in part to the upper body portion 504. Each of the upper body portion 504 and the lower body portion 503 may comprise a plurality of fabricated segments that may be assembled together to form the respective portion. Each segment may further comprise a plurality of components including, for example, an outer shell, an inner shell, and an insulating component disposed between the outer shell and the inner shell. The shells may be fabricated through a molding process, such as injection molding, blow molding, and the like. Each segment may be constructed with attachment points that are disposed to facilitate attaching the segments of a portion to form the completed portion (e.g., several segments may be attached together to form the lower body portion).

Approximate dimensions of a representative embodiment of the float tank depicted in various figures of this specification are show here:

| Dimension (mm) | Dimension Name and Figure Reference |
|---|---|
| 1990 | CLOSED DOOR TANK DEPTH 502 |
| 2650 | OUTSIDE LENGTH 602 |
| 1430 | TANK HEIGHT 604 |
| 2390 | FLUID FLOAT LENGTH 608 |
| 1160 | DOOR HEIGHT 610 |
| 250 | FILL LEVEL HEIGHT 612 |
| 2650 | TANK WIDTH 802 |
| 1320 | DOOR OPENING WIDTH 804 |
| 1040 | DOOR OPENING DEPTH 808 |
| 2100 | OPEN DOOR TANK DEPTH 810 |
| 1840 | TANK BODY DEPTH 902 |
| 260 | DOOR EXTENSION 904 |
| 500 | THRESHOLD HEIGHT 908 |
| 1610 | HEIGHT OF DOOR WHEN OPENED 910 |
| 1380 | HEIGHT OF TANK WITH DOOR OPENED 912 |

A float tank as described and depicted herein may be designed to achieve a high degree of manufacturability and operational capabilities. The float tank of the present disclosure incorporates aspects such as smooth curved surfaces, large radius corners, few planar surfaces, modular construction, and the like. The tank may be constructed of a plurality of modular sections that interlock to form the overall shape. At least a lower body portion 503 of the tank may be separable from an upper body portion 504. The lower body portion 503 may be constructed to allow inverted nesting of the upper portion 504 for shipment or storage. Likewise, a plurality of base portions may be nestable.

The tank may be constructed with condensation resistant hydrophobic coating. The floor may be configured with non-slip features. The tank may include grab handles.

Ventilation may be achieved through passive air exchange portals that permit safe passage of air between the interior and exterior while mitigating light and sound passage.

Insulation in the tank walls may reduce exterior sound transfer. Mating of the door with the tank walls may prevent exterior light from entering the float tank housing, while allowing passive convection air exchange.

In an embodiment, mating of the door to the body of the float tank may result in an indirect air flow path along a portion of the lower edge(s) of the door and along a portion of the upper edge(s) of the door. Air inside the tank will tend to rise and exit the upper indirect air flow path. External air will replace this exiting air by passing through the lower indirect air flow path. A heating facility may be disposed to heat the external air so that it enters the tank within the tolerance of the air that is exiting. The lower indirect air flow path may comprise an indirect slot along substantially the entire lower edge of the door as it mates with the opening in the upper body of the tank. The slot may be uninterrupted and/or may be partially interrupted by an air flow filter and the like. The indirect air flow path permits air to flow from one side of the door (e.g. the exterior) to the other side of the door (e.g., the interior of the float tank) while preventing substantially all light from passing from one side of the door to the other.

Figure 6:
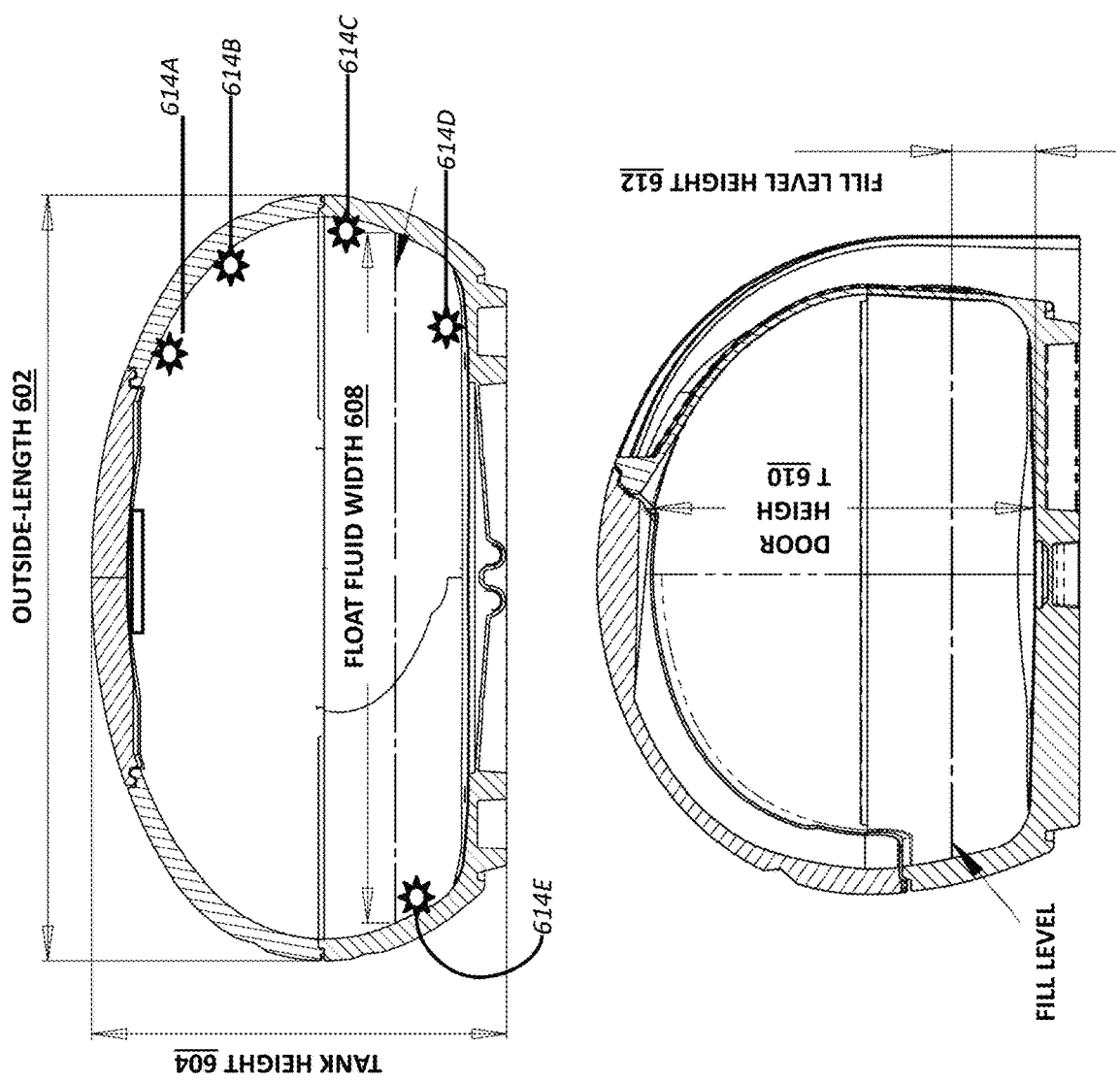
FIG. 6 depicts a cut away view of the embodiment depicted in FIG. 4.

Referring to FIG. 6 that depicts cut away views of the embodiment depicted in FIG. 5, the float tank may include a lighting plan that may include illumination sources. Sources of illumination may be disposed above the float fluid, such as sources 614A and 614B. Other sources may be disposed below the float fluid, such as along sides and/or ends of the float tank as depicted by sources 614C, 614D, and 614E. Any one or more of these sources of illumination may be computer controlled and the light emitted from any plurality of sources may be coordinated to produce a variety of lighting effects including, as an example, sunset-like lighting as the float session commences and/or sunrise lighting as the float session comes to an end. Lighting operational plans may be preconfigured, manually configured (e.g., through a user adjusting the light sources via a client user interface for the float tank system), automatically configured (e.g., derived from an audio file, such as a song), and the like. Lighting sources may be positioned along the inner walls, end panels, the top, on the bottom, or any other location within the tank.

Float tank representative dimensions that are listed above are depicted in FIG. 6 and include a float tank outside-length 602, a tank height 604, a fluid float zone length 608, a door height 610 and a float fluid level height 612.

Figure 7:
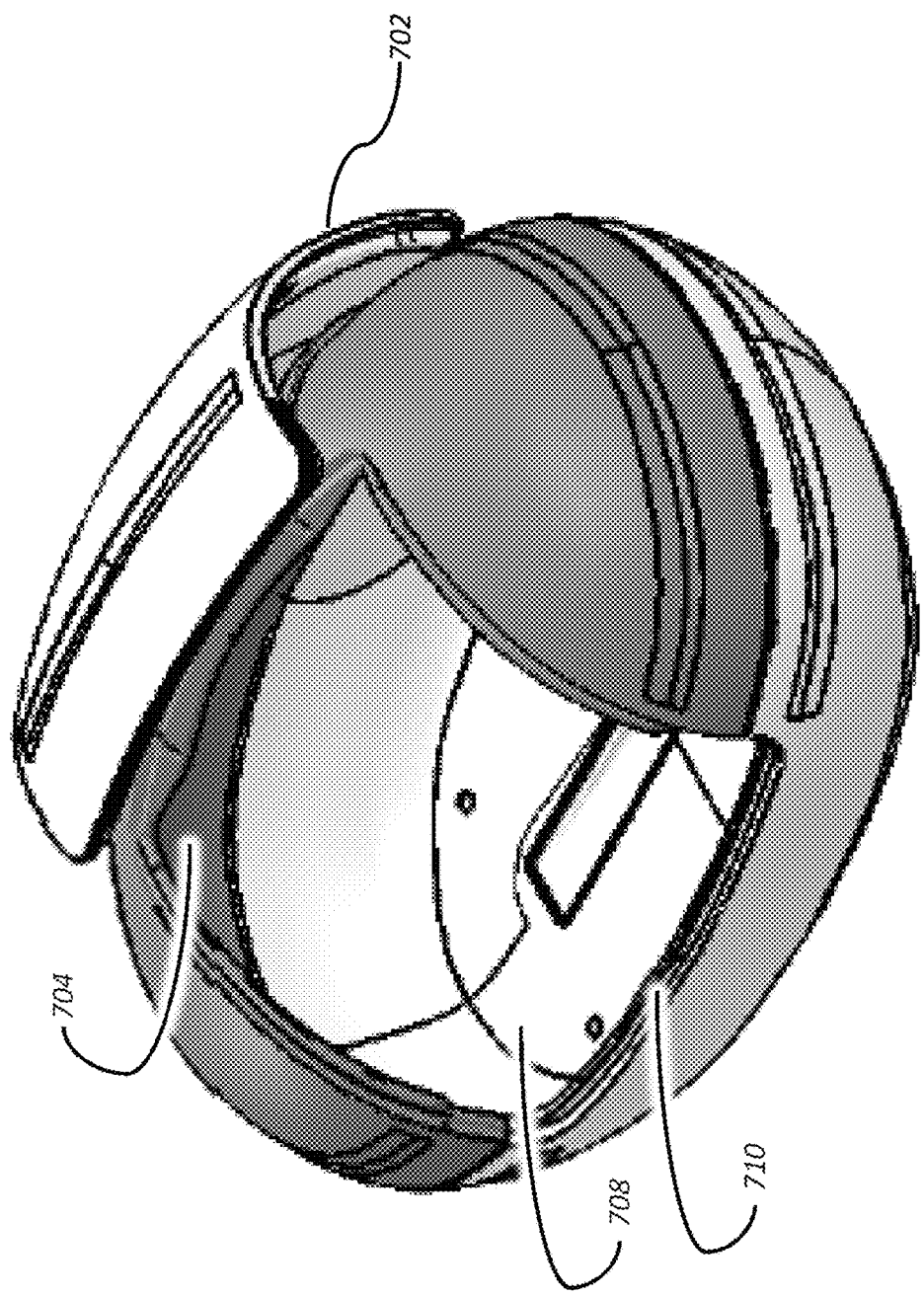
FIG. 7 depicts a top perspective view of an open-door embodiment of the float tank.

Referring to FIG. 7 that depicts a top perspective view of an open-door embodiment of the float tank, the open sliding door 702 reveals the inner float chamber upper portion 704 and the inner float chamber base portion 708. A lowered entry edge 710 of the base portion that provides a low step-over height is visible along the base portion where the door 702 would make contact when closed.

Figure 8:
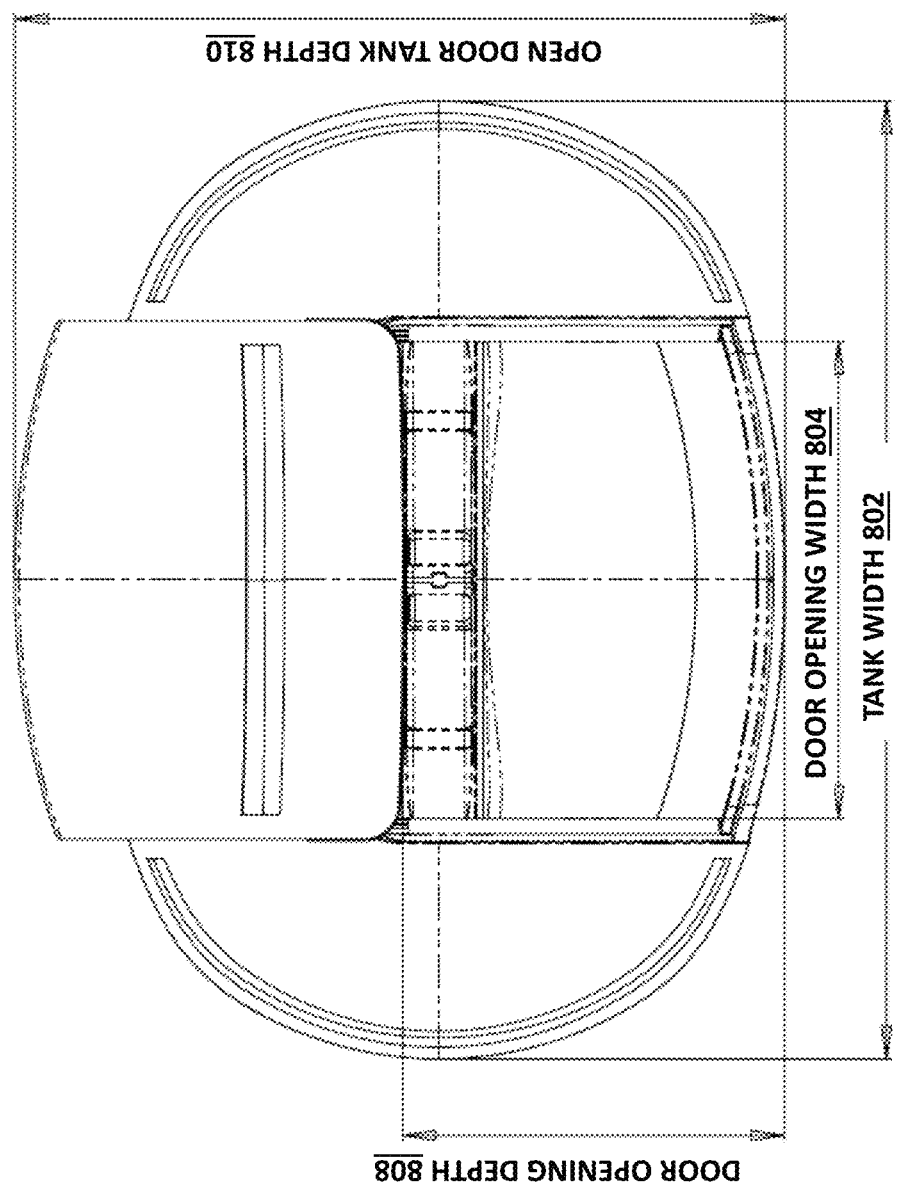
FIG. 8 depicts a top planar wire-frame view of the embodiment of FIG. 6 with typical dimensions.

Referring to FIG. 8 that depicts a top planar wire-frame view of the embodiment of FIG. 7, typical dimensions of aspects of the float tank are labeled. The dimensions depicted include door opening depth 808 that represents a distance from a front outer edge of the tank that is generally within the extent of an opening created by the door being opened to the nearest edge of the door. The dimensions include a door opening width 804, which represents an opening through, which a user can pass when entering or leaving the float tank. The dimensions further include a tank overall outer width 802 along a primary user float axis. The embodiment of FIG. 8 further includes a dimension that represents a depth of the tank when the door is opened (that includes the door) from the front edge of the tank to a backward extent of the door, this open door tank depth 810.

Figure 9:
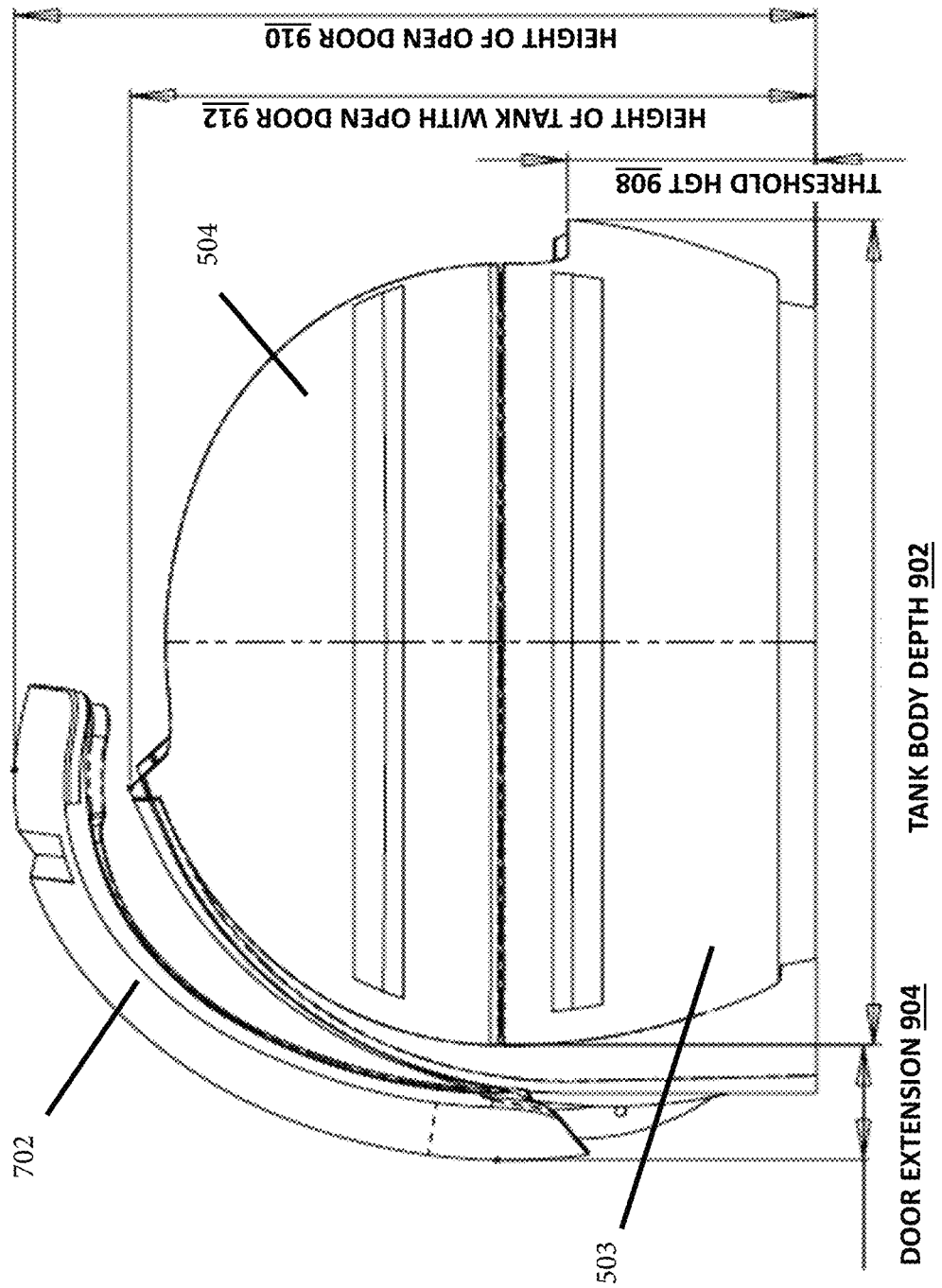
FIG. 9 depicts an end planar view of the float tank.

Referring to FIG. 9 that depicts an end planar view of the float tank with the door opened, typical dimensions of aspects of the float tank in this view are presented. The dimensions depicted include tank body depth 902 that represents an outer dimension of the tank from a front-most edge below the door opening to a back edge of the tank. The dimensions depicted further include a door extension 904 distance that represents the extent to which the door, when opened, extends beyond the back edge of the tank. Threshold height 908 represents a step-over height for entering and exiting the float tank through the opening created by the open door. A height of open door dimension 910 represents a distance from an outer bottom surface of the tank to a tallest external point on the opened door. A height of the tank with the door open 912 represents a distance from an outer bottom surface of the tank to a highest point on the tank upper body.

Figure 10:
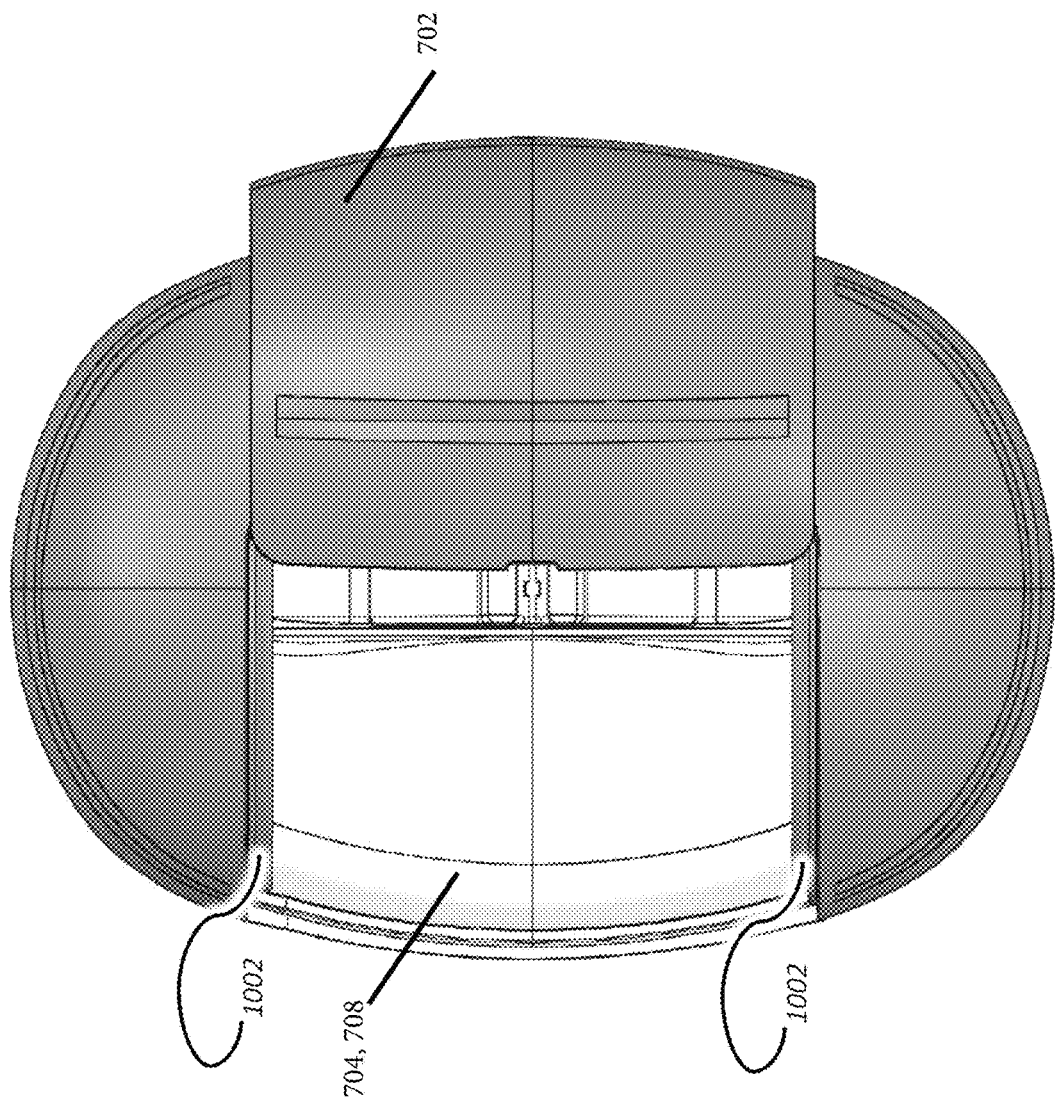
FIG. 10 depicts a top solid model view of the float tank.

Referring to FIG. 10 that depicts a top solid model view of the float tank with the sliding door opened, the inner float chamber 704, 708 is revealed. Flanges 1002 along the edges of the opening for the sliding door that facilitate securely closing the door to reduce light and sound transfer between the interior and exterior of the tank are depicts.

Figure 11:
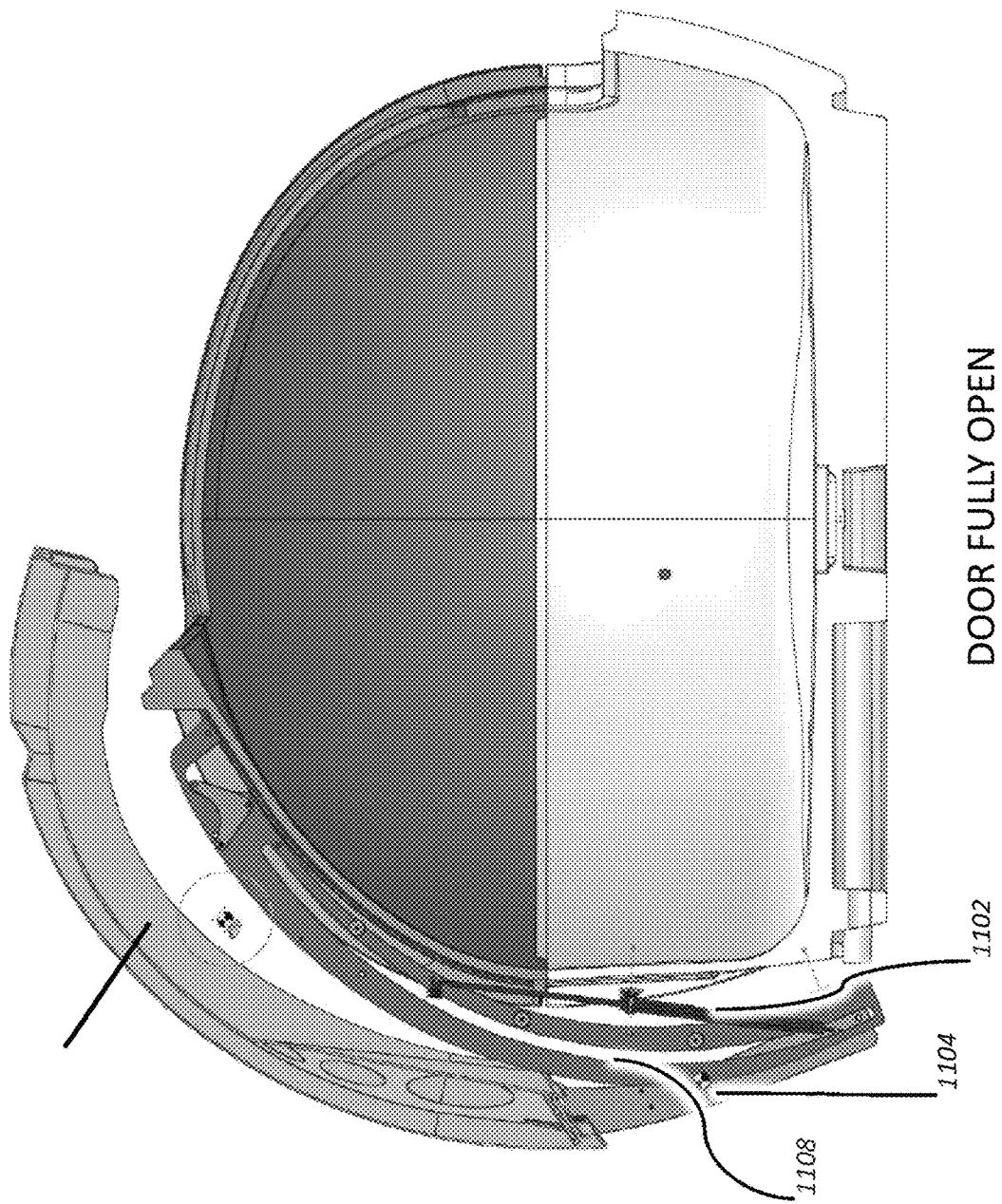
FIG. 11 depicts a cut-away end view of a fully open-door embodiment of the float tank with door mechanism details.

Referring to FIG. 11 that depicts a cut-away end view of a fully open-door embodiment of the float tank includes a few exemplary door mechanism details. In this embodiment of the door mechanism, a tension bar is depicted 1102 that provides stability when operating the door. A door support panel 1104 and a slotted door support panel guide element 1108 are also depicted.

Figure 12:
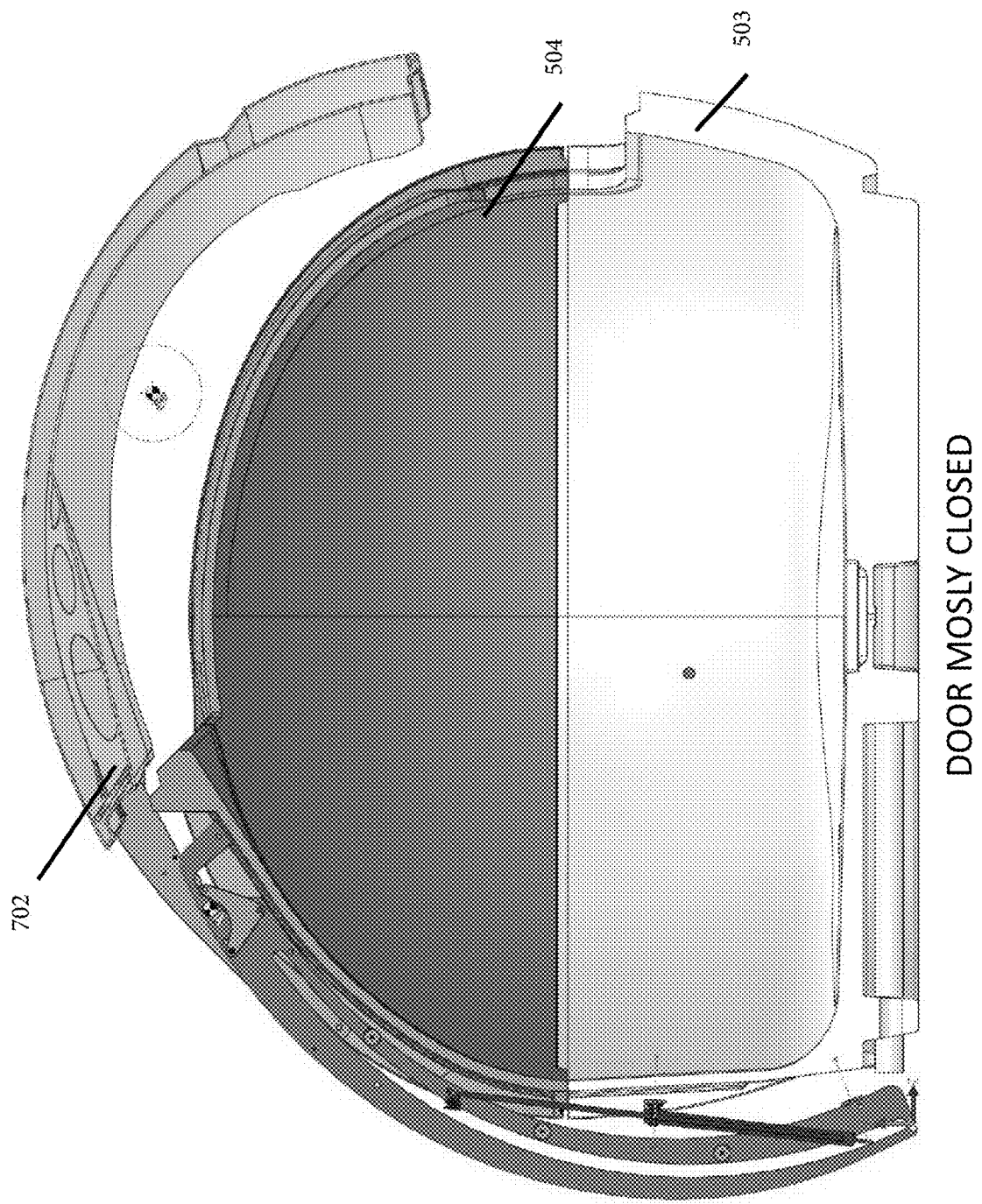
FIG. 12 depicts a cut-away end view of a partially open door embodiment of the float tank with door mechanism details.

Referring to FIG. 12 that depicts a cut-away end view of a partially open door embodiment of the float tank shows similar door mechanism details comparable to those of FIG. 11; however in this embodiment the door is almost fully closed.

Figure 13:
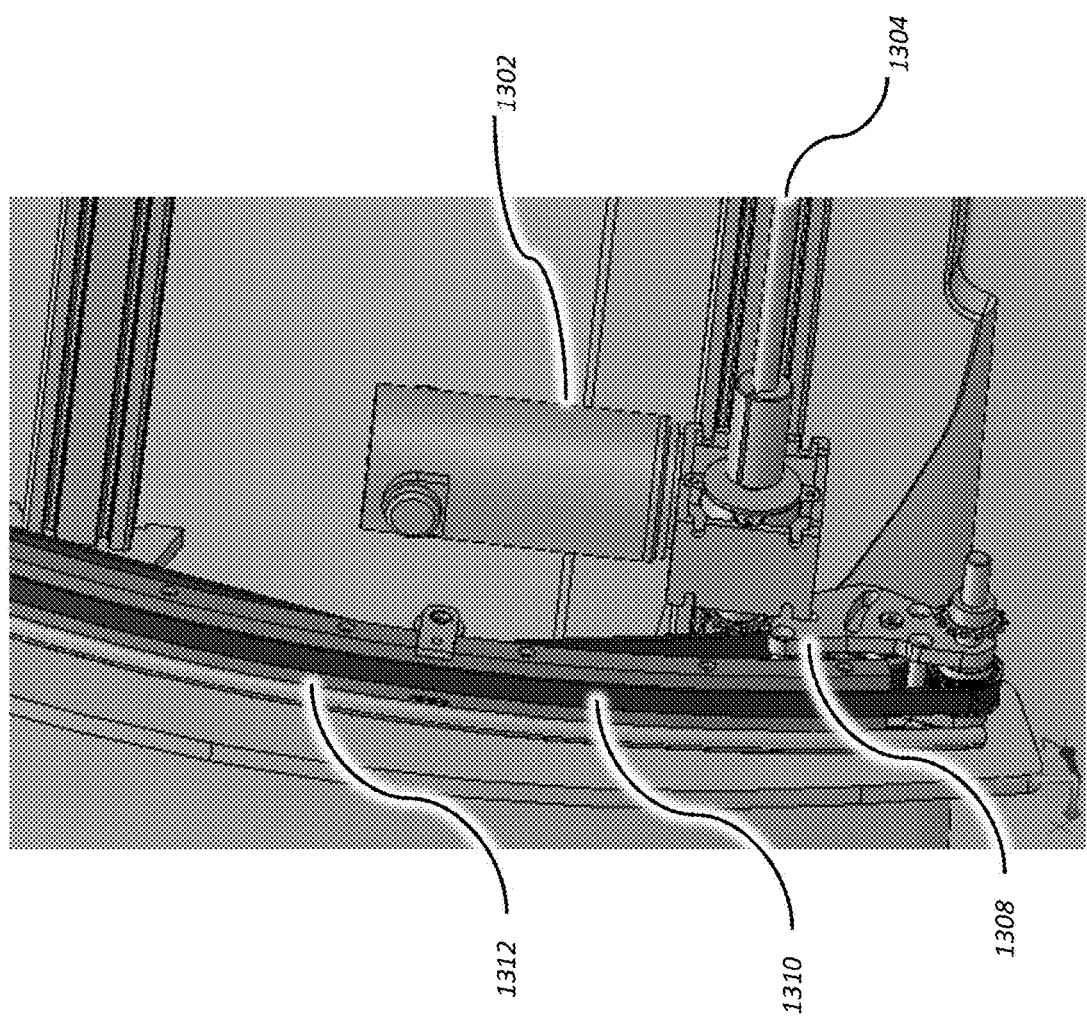
FIG. 13 depicts a perspective view of a door open/close mechanism.

Referring to FIG. 13 that depicts a perspective view of a door open/close mechanism embodiment, details of a belt or driven system are depicted. In the embodiment of FIG. 13, a motor, such as an electric or other type of motor 1302 turns a substantially vertical shaft that is converted into rotational motion around a horizontal shaft 1304. At each end of the horizontal shaft is disposed a gear and belt drive assembly 1308 that transfers the motor's output to a belt 1310. The belt is attached to a belt carrier 1312 that is further attached to a moveable portion of the door (not shown). As the motor operates, the belt moves either clock-wise or counter-clock-wise to open or close the door. The door moves due to the movement of the belt that is attached to the door through the belt carrier 1312. A corresponding set of belt drive elements 1308, 1310, 1312 are disposed at the other end of the horizontal shaft to operate cooperatively to open and/or close the door. Control of the door may be computerized and controlled from a user interface, operational interface, and the like.

Figure 14:
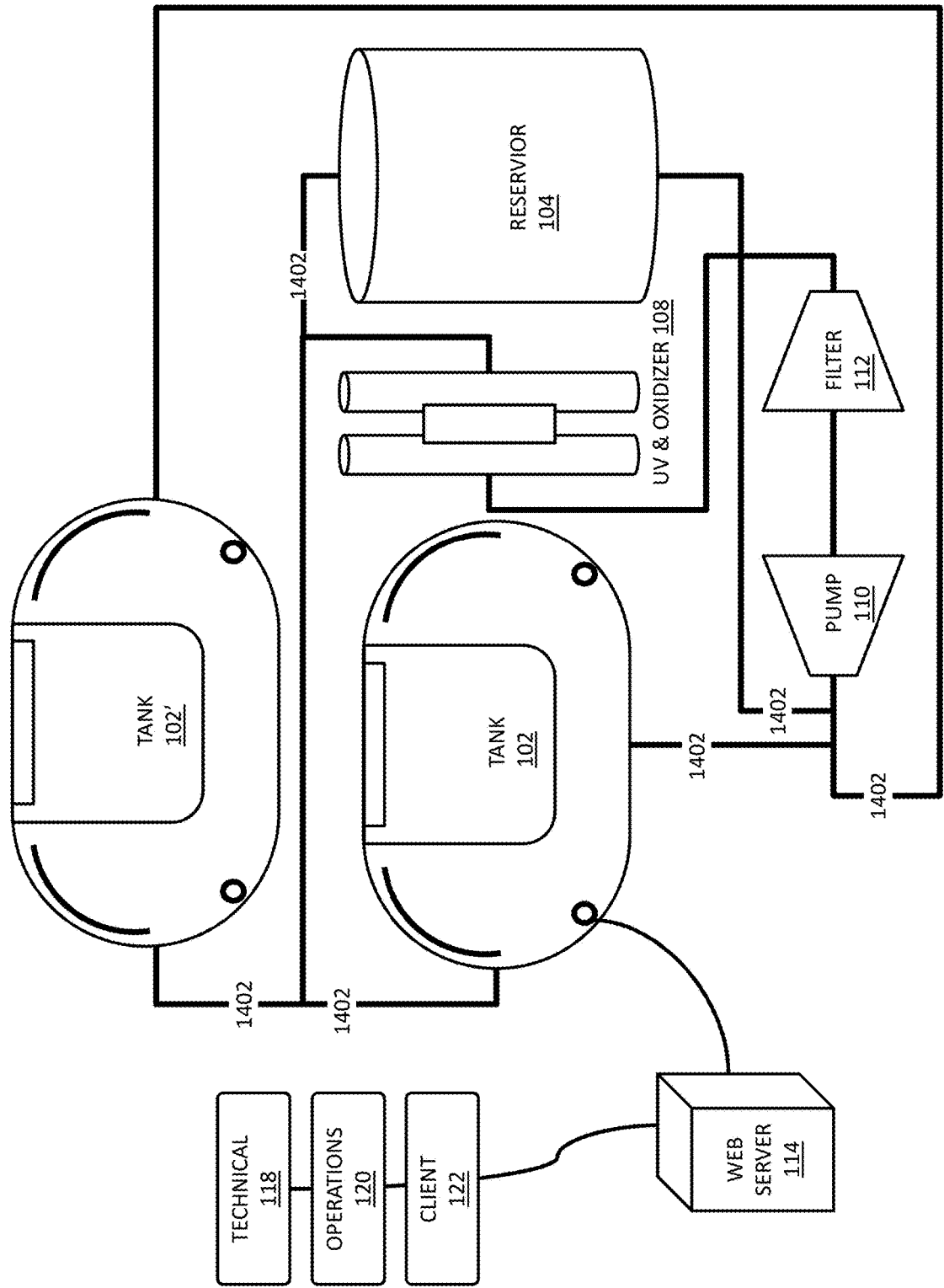
FIG. 14 depicts a schematic view of a multiple float tank embodiment of the float tank system described herein.

Referring to FIG. 14 that depicts a schematic view of a multiple float tank embodiment of the float tank system, a single reservoir may be shared with a plurality of float tanks. Cleanliness of each tank is controlled by allowing either tank to flow through the filtering systems 112 and the UV & oxidizer 108 each time a tank is filled or emptied. Active valving at various points 1402 may be computer controlled (e.g., such as by webserver 114) to enable filling one or two tanks from the reservoir or emptying one or two tanks to the reservoir. In the embodiment of FIG. 14, reservoir 1404 may have approximately twice the capacity of reservoir 104 as depicted in at least FIG. 1 herein.

Referring to FIG. 15 that depicts end and side views of an embodiment of an ultraviolet filtration subsystem 108 may provide active filtering and germicidal action on the float fluid. The ultraviolet filtering system of FIG. 15 may include an active dual pass UV germicidal disinfection unit that may include use of short-wavelength ultraviolet light that may kill and/or deactivate microorganism by destroying a nucleus and/or disrupting the DMA of such microorganisms leaving them unable to perform vital cellular functions. Further details of this process are depicted in FIG. 16.

Figure 16:
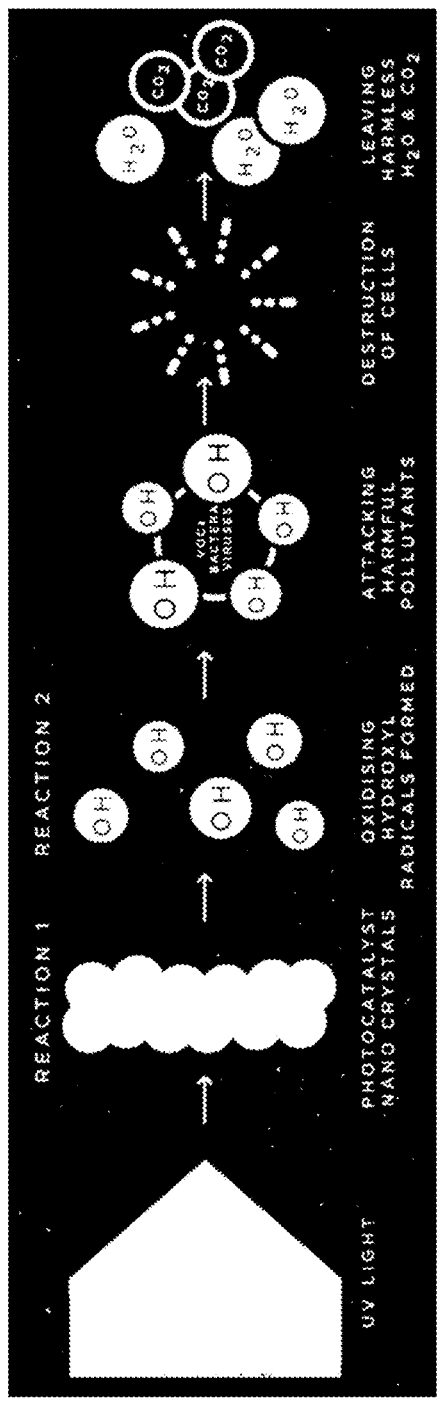
FIG. 16 depicts details of a photocatalytic hybrid UV hydroxyl oxidizer reaction process.

Referring to FIG. 16 that depicts details of a dual pass photocatalytic hybrid UV hydroxyl oxidizer reaction process in which oxidizing hydroxyl radicals are formed in the float fluid where they attack harmful pollutants, bacteria, viruses, and the like to perform a cellular disruption process that leaves behind only harmless water and carbon dioxide in the float fluid.

Figure 17:
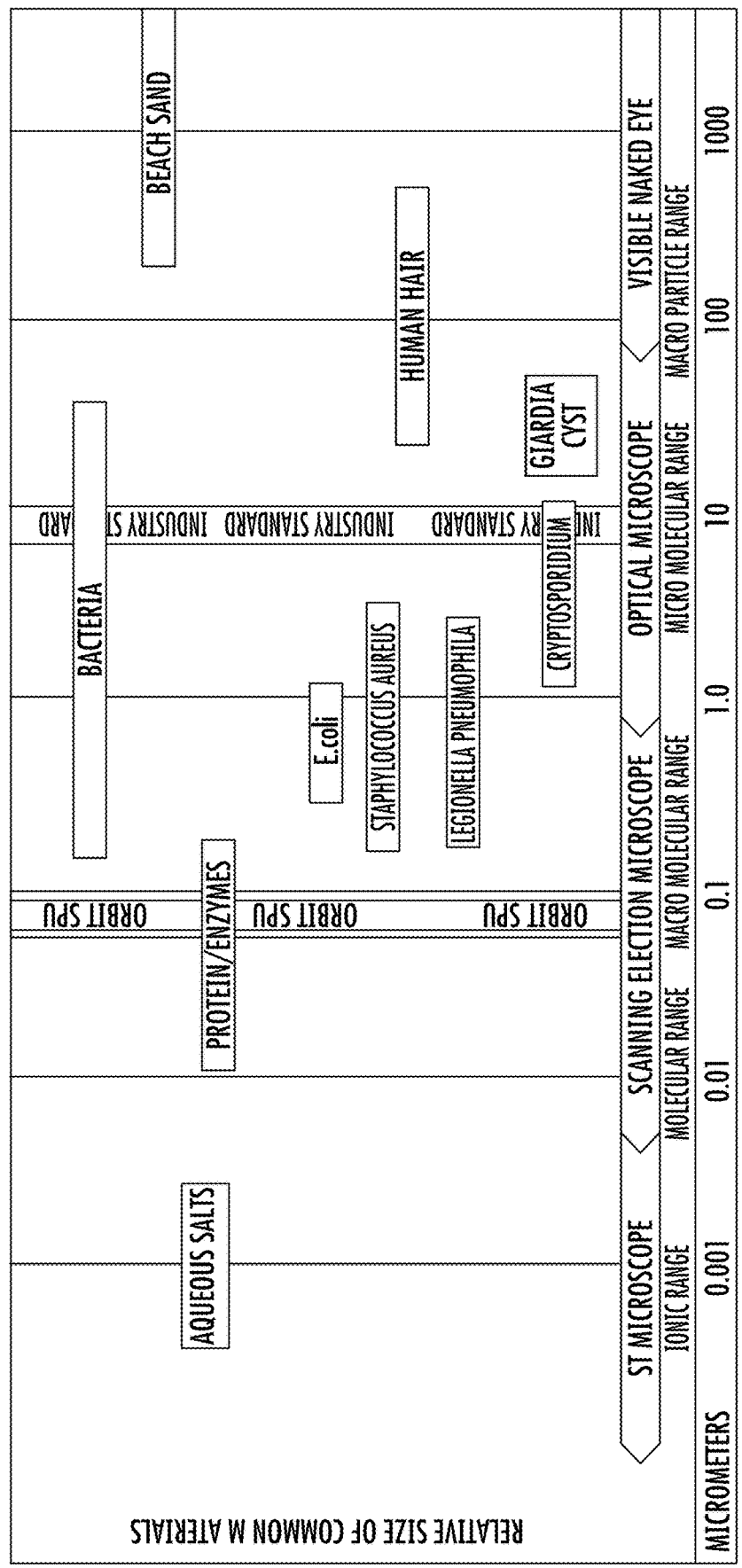
FIG. 17 depicts filter operation on a scale of relative size of common materials being filtered.

Referring to FIG. 17 that depicts filter operation on a scale of relative size of common materials being filtered, a sub-micron filtration element particle filtering size, such as filter 112 is depicted. In this exemplary filter embodiment, particle sizes greater than 0.1 micrometers are filtered out of the float fluid, allowing only some proteins and/or enzymes to remain in the float fluid.

Figure 18:
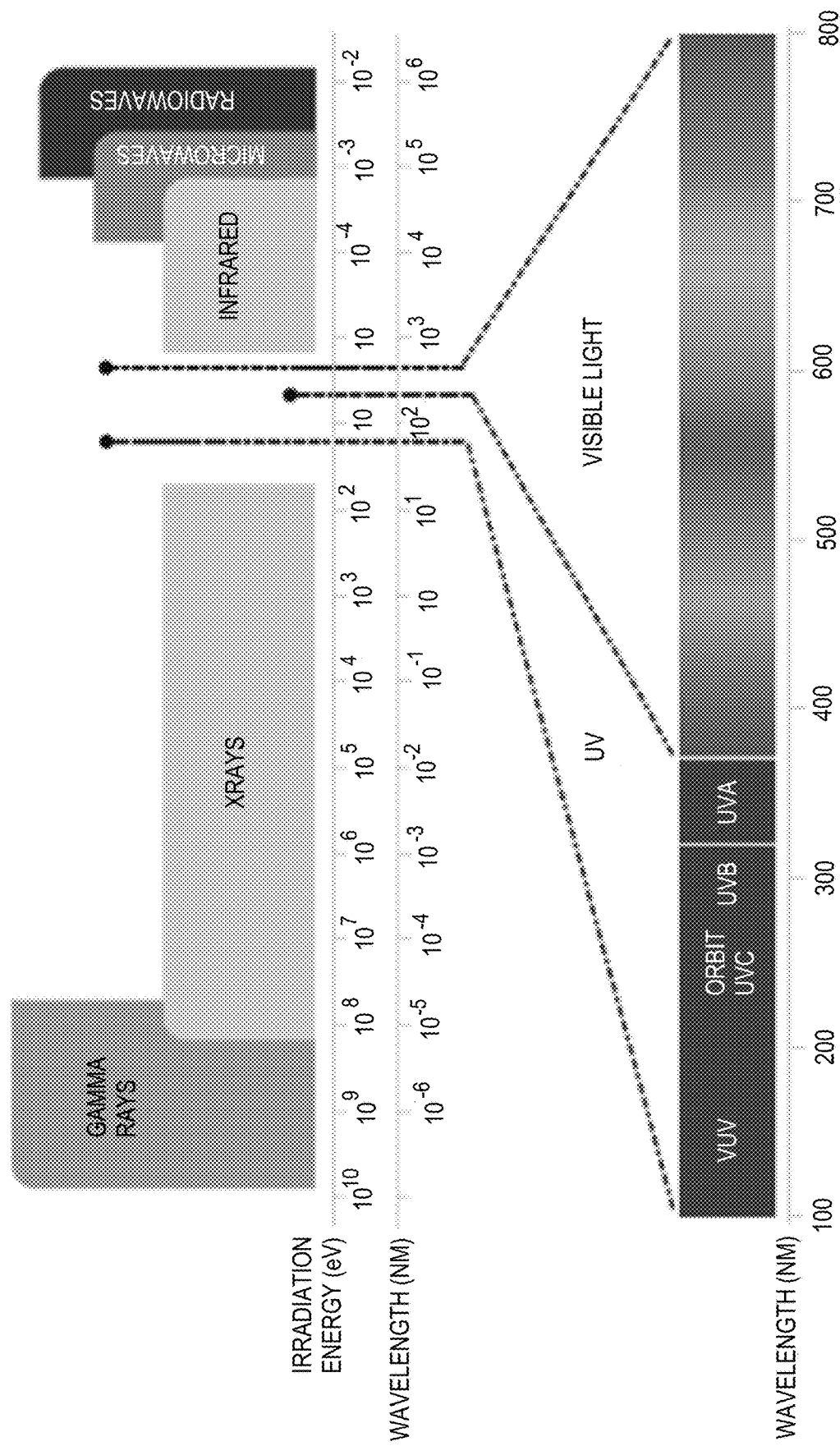
FIG. 18 depicts light wavelength irradiation energy spectrum with positioning of the UV filtering capability of the float tank system.

Referring to FIG. 18 that depicts a light wavelength irradiation energy spectrum and the relative positioning of the UV filtering capability of the float tank system, exemplary wavelength used in the float tank UV filtering system may fall in the general range of 200-275 nanometers, comparable to the UVC spectrum.

Figure 19:
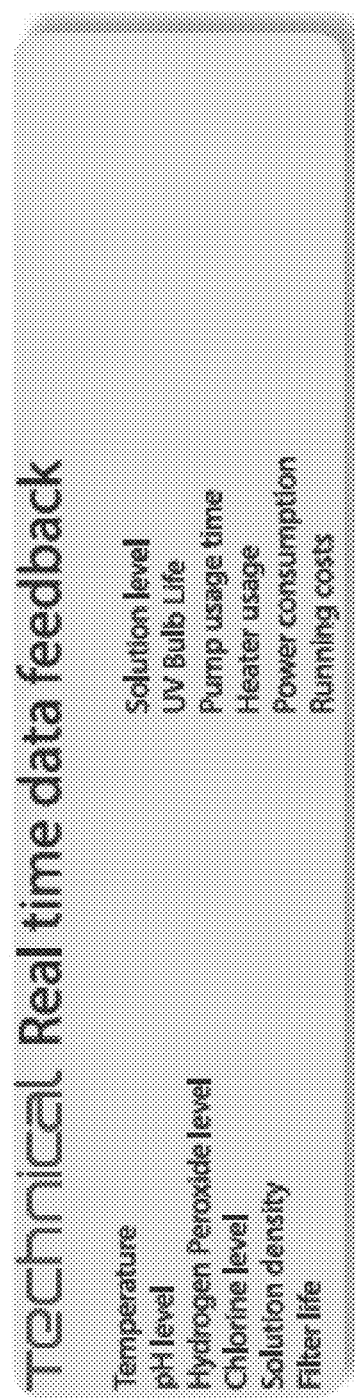
FIG. 19 depicts a diagram of a technical user interface feature set.

Referring to FIG. 19 that depicts a screen shot of a technical user interface, real-time data and feedback may be provided in such a technical user interface. Aspects of the float tank system may be presented and controllable through a technical user interface, such as float fluid temperature, float tank interior air temperature, pH level, hydrogen peroxide level, chlorine level, solution density, filter life, solution level, UV bulb life, pump usage time, heater usage, power consumption, running costs, and the like.

Figure 20:
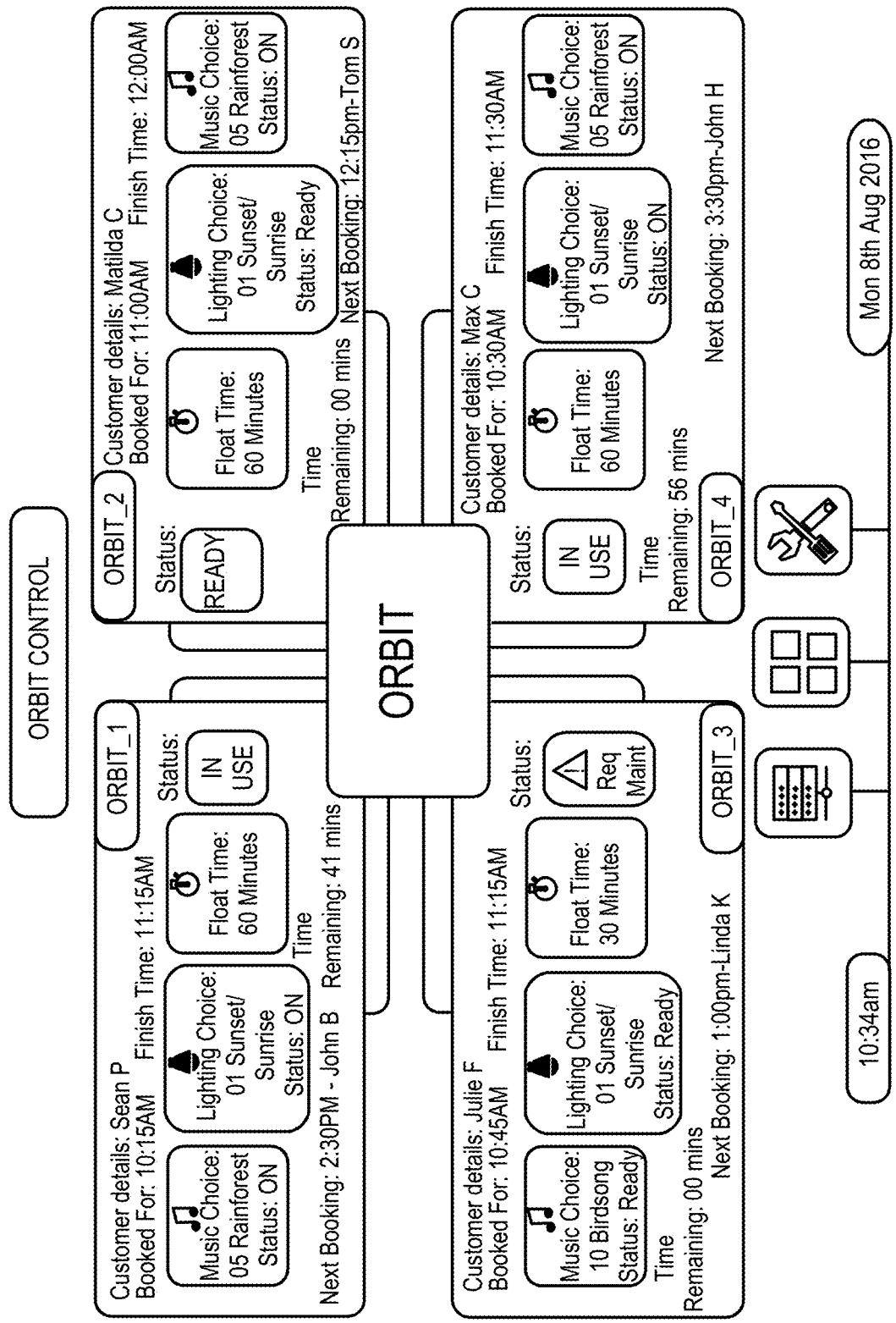
FIG. 20 depicts an example of a screen shot of a multi-tank operations user interface.

Referring to FIG. 20 that depicts an example of a screen shot of an operations user interface, various float tank system operational content may be presented and accessible, including float session time parameters (e.g., time in float, time to next float session, etc.), temperature control of the float fluid, interior tank air temperature, external ambient air temperature, music selection and volume, lighting mode, client status (standing in/out of the tank, floating, etc.), manual or automatic start based on client explicit indication of ready to float, detected presence of client in float position, enclosure door status, float fluid status, and the like. It should be noted that the layout and the specifics of the interface can vary from what is presented.

Figure 21:
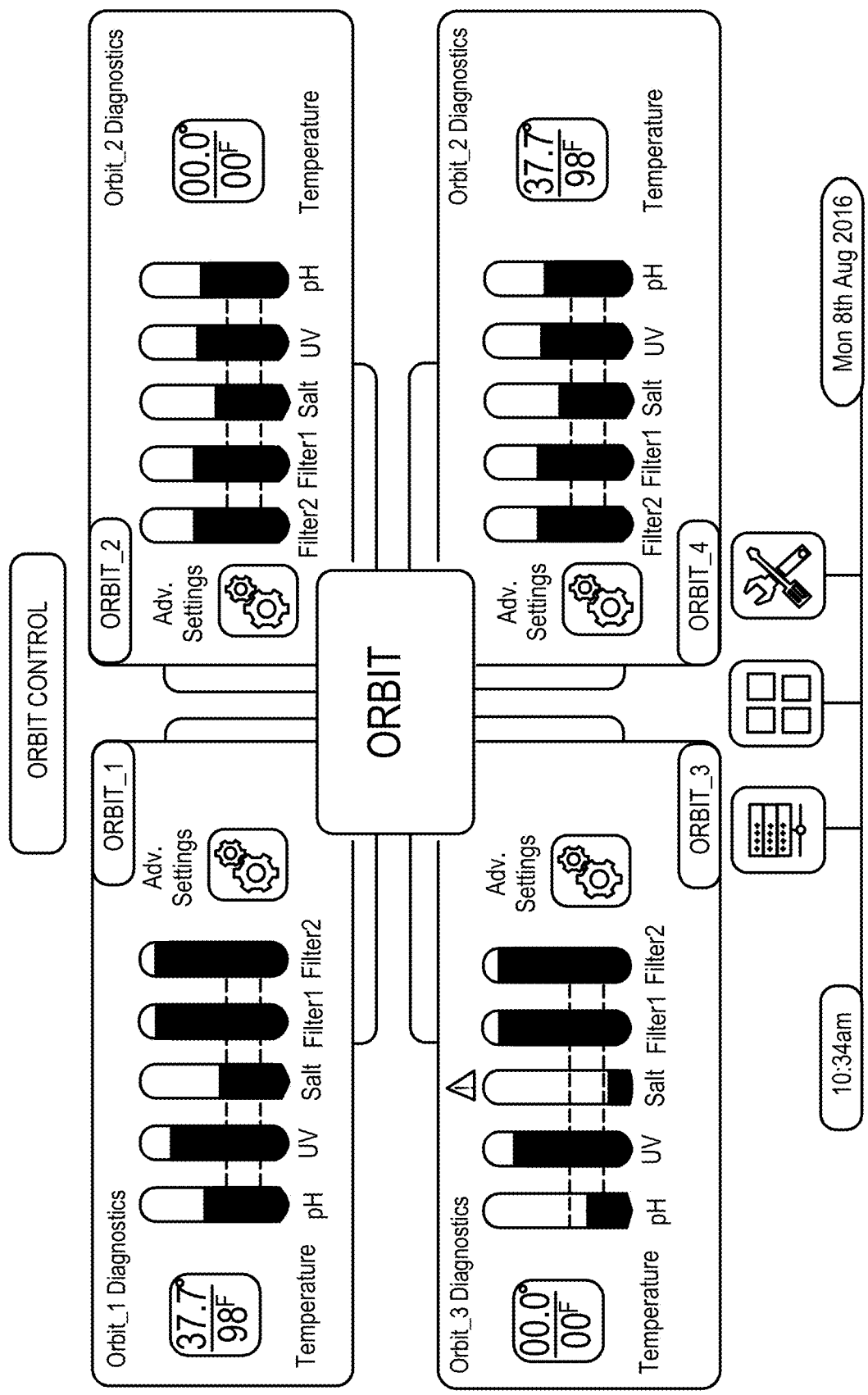
FIG. 21 depicts an example of a diagnostics screen shot of a multi-tank operations user interface.
Figure 23:
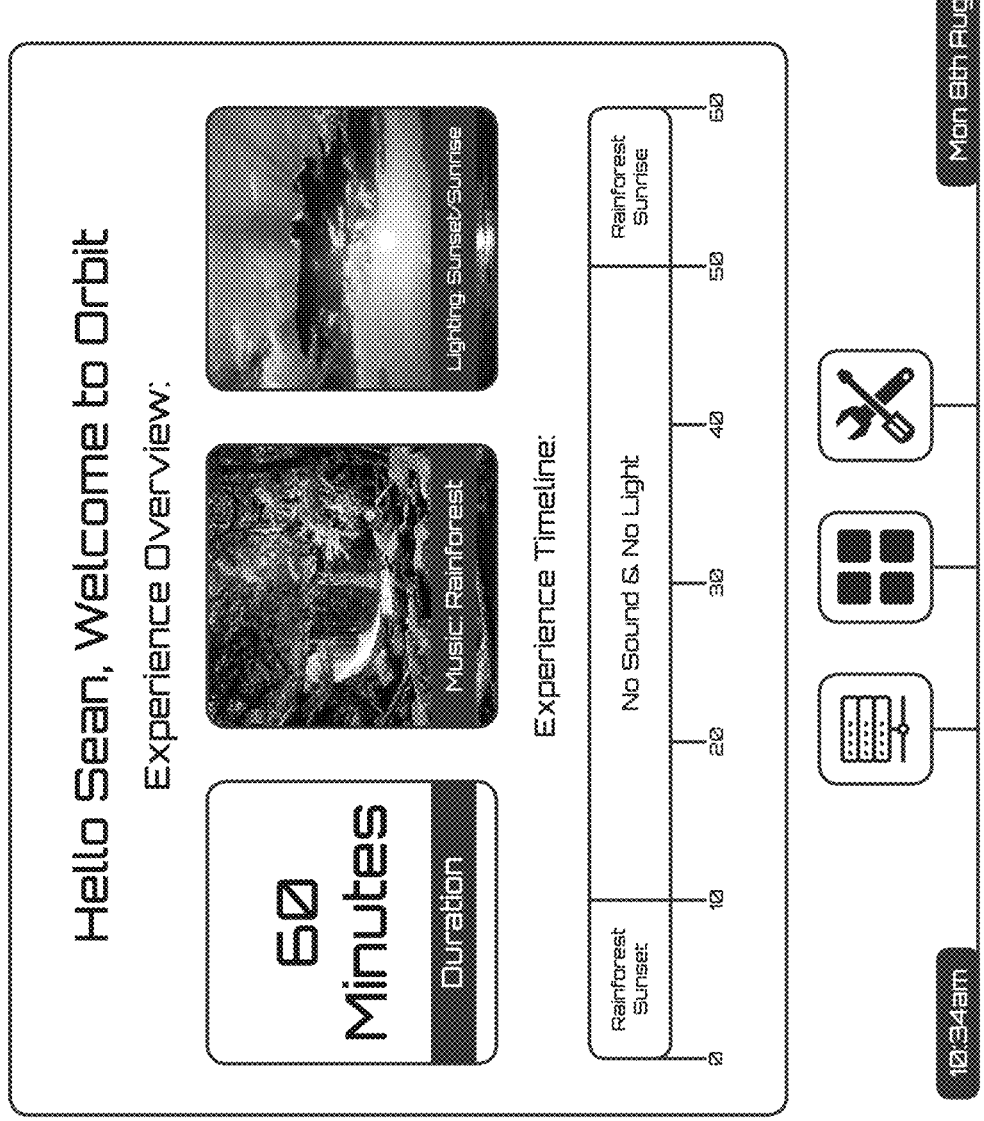
FIG. 23 depicts an example of a screen shot of a client's user interface.

Referring to FIG. 21 and FIG. 23 that depict an example of a screen shot of a client's user interface, user customization may be accomplished and made available to the user. A client interface may be presented on the client's personal mobile device, a dedicated electronic display proximal to the float tank, and the like. The client interface may include a touch screen that may be environmentally protected from water, and the like. A client interface may be configured to display a client's name and/or other identifying information for a float session. Additionally client preferences, such as settings for music, lighting, and the like may be presented to be (optionally) verified by the client. Additionally, a client interface may present recommendations for products, services, music, lighting, new features of the float tank or session, and the like. These recommendations may be based on data gathered from other uses. It should be noted that the layout and the specifics of the interface can vary from what is presented.

In addition to the computer monitoring and control described herein, an on-line portal that facilitates access for operators and users of a float tank system may be provided. Through such a portal, an operator may control automatic consumables (e.g., filters, UV bulbs, and the like) delivery. Automated delivery may be based on a schedule, on monitored consumable status (e.g., filter quality), may incorporate operator preferences, may be based on aggregated consumables history for a plurality of float tanks within and across operational centers, may be based on consumables life expectancy (e.g., manufacturer published filter life cycles). Such a portal may facilitate booking float sessions, adjusting individual account settings, preferences (e.g., illumination, audio, video, and the like), generating and applying deals and promotions plus administering a customer loyalty program, and the like.

Additional features of the float tank system may include a mist spray or accessible spray tube that allows a user to clear his/her face of the float fluid or other condensation. Hypnosis focus points may be added to the interior surface of the float tank top and/or door. An aroma control system that may produce scents of a user's choice may be provided. Images, such as clouds, night sky and the like may be projected on the ceiling (e.g., inner surface of the float tank top). Air bubbles may be injected into one or more ports in the float tank floor. A towel may be connected to a spring-line cord (e.g. Bungee) that may be attached to the interior portion of the float tank top may be accessible to the user. A fan that is variable speed and can be positioned and directed by the user may be configured in the interior of the float tank.

Figure 22:
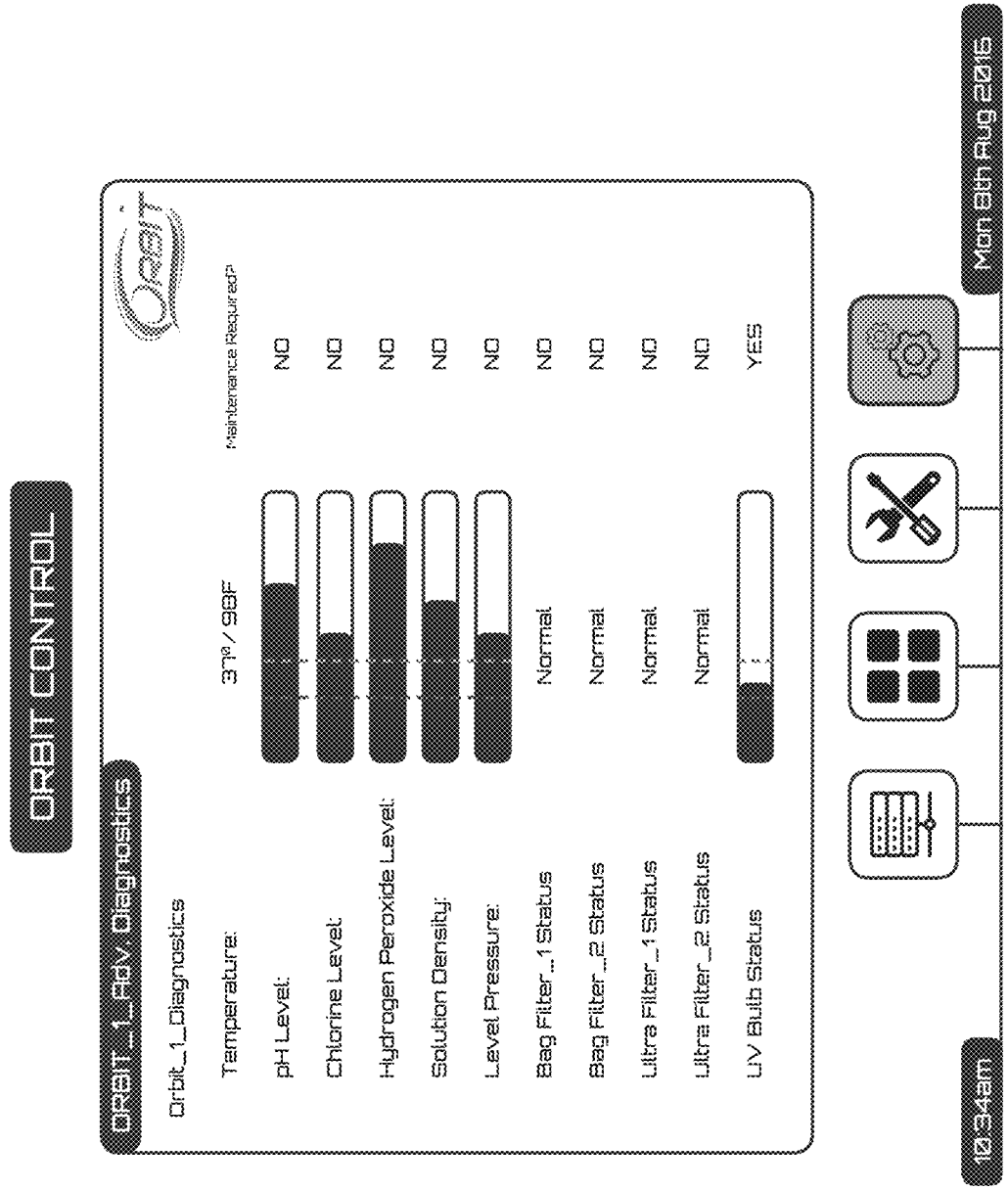
FIG. 22 depicts an example of an advanced diagnostics screen shot of an operations user interface.

FIG. 22 shows a screenshot of advanced diagnostics available for monitoring of the float tank system. The diagnostics monitored may be, but is not limited to temperature, pH level, chlorine level, hydrogen peroxide level, solution density, level pressure, bag filter status, ultra filter status and UV bulb status.

Figure 24:
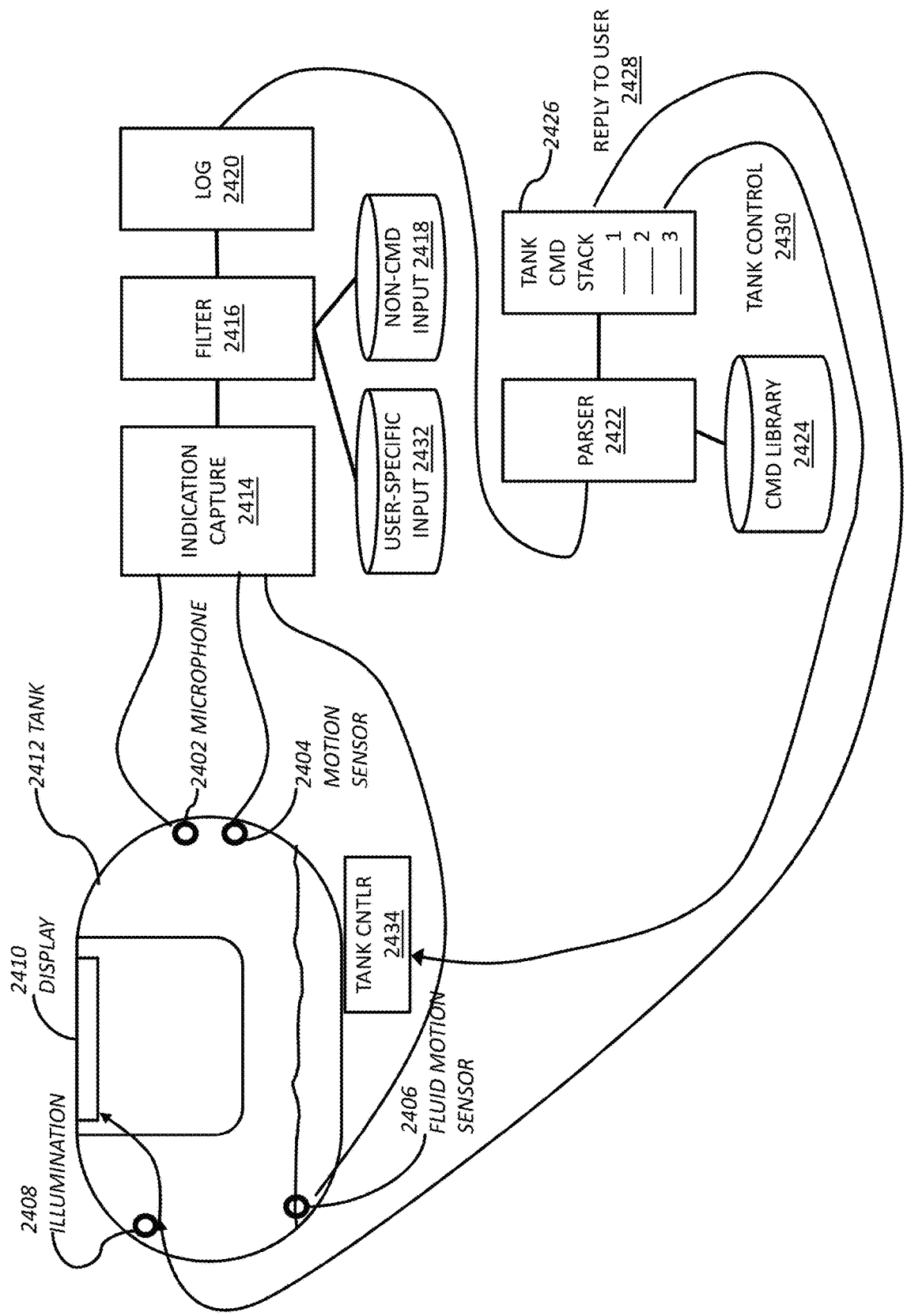
FIG. 24 depicts a diagram of elements of a sensory deprivation float tank non-tactile control detection and processing system.

Referring to FIG. 24, an embodiment is depicted for detecting, processing, and activating a float tank command in response to a user indicating via verbal command or body/appendage movement a desire to interact with the tank controller.

A float tank 2412 may be configured with various sensors, such as an audio sensor 2402, an above-fluid motion sensor 2404, a fluid motion sensor 2406 and the like. These sensors may be monitored by a processing facility to look for sounds and/or movement that is indicative of a user communicating to a control system of the tank. An illumination or lighting system 2408 is present within the float tank 2412.

The audio sensor 2402 may be a microphone or an array of microphones to facilitate detecting and isolating sounds occurring in the tank. Sound occurring in the tank may be associated with phases of a flotation session and or a current state of flotation tank control aspects. In an example, a current phase of a flotation session may include generating audio to transition a user from a sensory deprived state to an awake state nearing the end of a flotation session. A current state of flotation system control may include introduction of gas bubbles to the flotation fluid, resulting in rumbling or bubbling sounds. Isolating multiple sounds may also be important because the tank may include ambient music, audio associated with a video on a display screen, pump or other sounds, and the like, some of which may be present during certain phases of the flotation session, but not during other phases. Multiple microphones, such as a microphone array, may facilitate determining a source location of the sounds so that sounds that come from a location that is consistent with a user of the tank in a float or sitting position may be prioritized for capture over sounds from other locations in the tank.

The motion sensor 2404 may be configured as any of a range of motion detectors, proximity detectors, cameras, and the like. The motion sensor 2404 primary goal is to detect movement within the tank above the fluid level. The interpretation of such movement may be performed by a filtering and command processing facility described elsewhere herein. However, the motion sensor 2404 may be configurable to detect all motion but only report motion that conforms to select types of motion signature or intensity, such as a user moving his arm high in the tank or moving his hand laterally, etc. In this way, smaller motion, such as a user adjusting his float position or involuntarily sneezing and the like may be ignored by the motion sensor 2404. Alternatively, such determination may be performed by the filtering and processing facility noted above.

The fluid motion sensor 2406 may detect and report movement of the fluid. Similarly, to the motion sensor 2404, the fluid motion sensor 2406 may be configured to report certain types of motion, while ignoring other types of motion. As an example, fluid movement as a result of a user's reaching for a drying cloth or to itch his nose may be ignored. Also, similarly to the motion sensor 2404 description above, such discrimination of motion may be performed by a filtering and processing facility to which the fluid motion sensor 2406 reports. A movement of the fluid may be detected as an indication by a user of a desire to communicate with the tank control facility and/or the tank operator. As an example, if a user moves his hands to cause a swirling motion of the tank fluid, the user may be indicating a request for the tank controller 2434 to perform an action such as to increase the volume of the audio, and the like. A user fluttering of a foot or hand may result in a detectable fluid motion that may signal a different interaction with the sensory deprivation float tank control system.

Data from sensors 2402, 2404, and 2406 may be captured by an indication data capture facility 2414. This captured data may include one or more set of data that represent indications of a user interacting with a float tank control facility, such as to adjust an aspect of the float tank control, receive float-session status-related information, perform Internet queries, maintain or set new appointments for float tank sessions and the like. The data capture facility 2414 may capture various streams of data from the sensors (e.g., 2402, 2404, 2406) and adapt them to facilitate filtering so that only data sets from the sensor that are consistent with a command and the like are stored in a log. Adapting the streams may include adding a start/stop data stream indicator that facilitates a filter facility 2416 determining which sets of captured data are candidates for indicating a float tank interaction command.

The float tank indication filter facility 2416 may reference libraries of command input differentiating data and process the captured indication data sets with entries on the reference libraries to determine for each captured data set if it is a candidate for a command indication. Additionally, the libraries may contain key phrases that indicate a command may be received from the user after the detection of the key phrase. Therefore, a key phrase is a portion or keywords of a phrase which are identified as an indicator which precede a command. The filter facility may reference a non-command input library 2418 that may include characterizations of sounds, movements, and the like that do not correlate to float tank commands. By comparing captured input data with such libraries, ambient sounds, human generated sounds, such as snoring, whistling, and the like may be separated and discarded. Likewise, the filter facility 2416 may reference a user-specific input indication library 2432 for discerning which captured data sets represent possible float tank commands. A user input indication library 2432 may be beneficial because a user may prefer a gesture or sound for one or more float tank commands that may generally be considered a non-command input. The user-specific input library 2432 may be selected by referencing an identifier of the user of the float tank for the current float session.

The filtered candidate command indicators may be stored in a log 2420 with time stamps or the like to facilitate processing the log entries in the order in which they are received. This log 2420 may be processed chronologically. Although certain indicators may invoke a reordering of the log, such as an indicator that requires urgent control response, such as a command to open the tank lid and the like.

A command parser facility 2422 may access the log 2420 based on an algorithm, such as based on accessing the log entries in a chronological order. For each accessed indicator in the log, the parser facility 2422 may process the data associated with the indicator (e.g., an audio data set representative of audio data capture by the microphone 2402) with an algorithm that determines which, if any command in a command library 2424 the indicator is associated with. Once a command is determined, additional data, such as may be part of the indicator data set or may be captured as separate log entries, that may impact the execution of the determined command may be processed by the parser. The parser may determine if additional information is required to execute a determined command and parse the indicator log information accordingly. If the parser determines that a valid command is determined, but necessary configuration information is not available, such as if the user did not provide the required information or the user indicated two commands sequentially and the first command did not have sufficient information to process it, the user may be notified of such a discrepancy by video, audio, and/or physical stimuli in the float tank. As an example, the user may receive an audio message requesting the needed information, such as a temperature value if the parsed command is a "set air temperature" command, and the like.

The user may also receive an indication of the determined command via audio, video, illumination, and/or physical stimuli means. As an example, the user may request that the audio volume of the float tank be increased. The user may receive an audio message, such as "I understand that you would like the audio volume lowered. Is that correct?". The user may alternatively be presented with a video image or set of images that provides similar feedback. The message may be presented as a displayed text message rather than an audio message. Alternatively, the message may be presented graphically, such as by showing an audio volume slide being moved to a lower setting on the interior tank display screen 2410.

The parser 2422 may compose a command and configuration data set that is suitable for placing on a float tank command processing stack 2426 for execution by a tank controller 2434 or the like. Each command may be processed so that the audio and/or movement-originated commands are acknowledged to the user upon command activation, completion or both. As an example, a user in the float tank may receive an audio message when the user's determined audio command to tell the tank operator to extend the float by 5 minutes as been confirmed by the tank operator. In an automated tank control scenario, the audio command may be automatically acknowledged so that the user is notified once the float duration has been changed by the tank controller 2434. Data from the tank command stack may be retrieved by a tank controller 2434 as tank control command and meta data 2430. Likewise, a reply to a user 2428 may be retrieved from the tank command stack. The user reply 2428 may be configured as meta data for a tank control command 2430.

The sensors 2402, 2404, and 2406 may continuously monitor the interior of the float tank, such as during a float session to ensure that user indications of tank interaction are captured. However, the sensors may sample for audio, above fluid movement, and fluid movement continuously even outside of a float session; thereby providing the user with the option to command the tank before or after a float session duration. In this way, the user may use voice commands to set aspects of the float session, such as a playlist, ambient lighting, and the like.

The audio sensor 2402 may operate in a substantially dormant state until a wake-up command is detected, such as "Orbit" or the like. Similarly, an above fluid motion sensor 2404 may wake-up when an indication to do so is received, such as waving one's hand or raising one's foot and the like.

An example of monitoring, processing, and executing a float tank command based on an audio indication may include monitoring, with a processor audio in an environment proximal to the user while using the float tank. The processor may function as an intermediary between raw sensor data and the filter facility. In this example, the processor may operate an indication capture algorithm for indication capture facility 2414. Data retrieve from or delivered from sensors 2402, 2404, or 2406 may be processed into data sets that may be candidates for a user interacting with the float tank control. The candidates may be filtered by a filter facility 2416 that performs an algorithm that facilitates separating out sounds produced by the tank or because of a user movement within the tank from sounds associated with a user of the tank speaking. An indication log update facility 2420 may facilitate registering the sounds associated with a user of the tank speaking in a user interaction log. A parser 2422 may facilitate processing the user interaction log with a speech recognition processor thereby determining at least one of a command associated with an aspect of the float tank and one or more attributes associated with execution of the determined command. A tank command stack 2426 may be configured with speech-to-text commands for executing a float tank control program with the processor that controls the aspect of the tank based on the command and the one or more attributes. The user may receive feedback based on the occurrence of at least one of reception of the command, activation of the command, and completion of the command.

The audio sensors and movement sensors 2402, 2404, 2406 may each include separate processors which communicate with a controller 2434 of a computer control system.

By combining efficient manufacturing technology, design for user-centric comfort and accessibility with advanced automated operator control and operational features, the float tank methods and systems described herein provide clients with a personalized float experience and float facility owners with highly profitable and reliable equipment.

The present invention may include a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to illustrations and/or block diagrams of methods, apparatus (systems), and computer program products according to embodiments of the invention. It will be understood that each block of the illustrations and/or block diagrams, and combinations of blocks in the illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

What is claimed is:

1. A method of controlling an aspect of a float tank by a user of the float tank independent of a physical control interface of the float tank being accessible to the user, when the user is floating in the float tank, the float tank comprising a computer having at least a processor and an audio processor, comprising:
   monitoring, by the audio processor, in an environment proximal to the user in the float tank;
   separating out, by the audio processor, sounds produced by the tank, sounds of movement within the tank by the user, and sounds associated with the user of the tank speaking;
   registering, by the audio processor, the sounds associated with the user of the tank speaking in a user interaction log;
   processing, by the audio processor, the user interaction log with a speech recognition processor thereby determining at least one command associated with an aspect of the float tank and one or more attributes associated with execution of the determined at least one command;
   executing, by the audio processor, a float tank control program with a processor that controls the aspect of the tank based on the determined at least one command and the one or more attributes; and
   indicating, by the audio processor, to the user of reception of the determined at least one command, initiating of the determined at least one command, and completion of the determined at least one command.

2. The method of claim 1, wherein separating out, by the audio processor, sounds comprises the audio processor comparing registered sounds with a library of sounds that facilitate distinguishing between non-command sounds and potential command sounds.

3. The method of claim 1, wherein separating out, by the audio processor, sounds comprises the audio processor comparing registered sounds with a user-specific library of sounds that facilitate distinguishing non-command sounds from potential command sounds, wherein the user-specific library is based on a float-tank identity of the user.

4. The method of claim 1, wherein separating out, by the audio processor, sounds comprises the audio processor matching sounds detected through the monitoring with at least one of: audio being produced by the tank, echoes within the tank, sound associated with movement of float fluid into or out of the tank, sound associated with movement of the float fluid interfacing with interior surfaces of the tank, sound associated with user movement within the float fluid, and non-language-based user initiated sound.

5. The method of claim 1, wherein processing, by the audio processor, the user interaction log comprises the audio processor detecting at least one of word and phrases that correspond to a word or phrase that is associated with a float tank interaction command in a library of float tank commands.

6. The method of claim 1, wherein processing, by the audio processor, the user interaction log comprises the audio processor generating at least one set of tank control instructions comprising a tank command that corresponds to one of the determined at least one commands and at least one tank command attribute that corresponds to the determined one or more attributes.

7. The method of claim 1, wherein indicating to the user comprises at least one of an audio indication, a visual indication, and a tactile indication.

8. The method of claim 7, wherein the audio indication is one of a tone and a natural language utterance.

9. The method of claim 7, wherein the visual indication comprises one of a blinking light, a change in ambient light, a change in ambient light color, and a change to a portion of an electronic display screen.

10. The method of claim 1, further comprising a processor:
    monitoring, movement of physical objects in an environment proximal to the user in the float tank;
    registering, movement associated with the user of the tank moving at least one appendage in the user interaction log;
    processing, the user interaction log with the registered movement of the at least one appendage, thereby determining one of the determined at least one command associated with the aspect of the float tank and one or more attributes associated with execution of the determined at least one command;
    executing, the float tank control program controlling the aspect of the tank based on the determined at least one command and the one or more attributes; and
    indicating, to the user of reception of the determined at least one command, initiating of the determined at least one command, and completion of the determined at least one command.

11. The method of claim 10, wherein registering the movement comprises the at least one processor comparing registered movements with a library of movements that facilitate distinguishing between non-command movements and potential command movements.

12. The method of claim 10, wherein registering the movements comprises the at least one processor comparing registered movements with a user-specific library of sounds that facilitate distinguishing non-command movements from potential command movements, wherein the user-specific library is based on a float-tank identity of the user.

13. The method of claim 10, wherein processing the user interaction log comprises detecting movements that correspond to a float tank interaction command in a library of float tank commands.

14. The method of claim 10, wherein processing the user interaction log comprises the at least one processor generating at least one set of tank control instructions comprising a tank command that corresponds to one of the determined at least one commands and at least one tank command attribute that corresponds to the determined one or more attributes.

15. The method of claim 10, wherein indicating to the user comprises at least one of an audio indication, a visual indication, a tactile indication.

16. The method of claim 1, wherein processing, by the audio processor, the user interaction log with a speech recognition processor thereby determining one of the determined at least one commands associated with the aspect of the float tank and the one or more attributes associated with execution of one of the determined at least one commands further comprises detecting a key audio phrase from the sounds associated with the user in the float tank.

17. A sensory deprivation device configured with an audio sensor and a motion sensor disposed for detecting audio and motion within a flotation space of the sensory deprivation device, comprising:
- an interaction monitoring facility configured to detect a plurality of human utterances captured by the audio sensor that correlate to sensory deprivation device control commands;
- the interaction monitoring facility configured to detect at least one of user movement above a flotation fluid disposed in the flotation space and movement of the disposed fluid captured by the motion sensor, the detected user movement or movement of the disposed fluid corresponding to at least one of the sensory deprivation device control commands;
- a sensory deprivation device control interface in communication with the interaction monitoring facility that maps at least one of the human utterances captured by the audio sensor and the detected user movement or movement of the disposed fluid corresponding to flotation tank control commands as a mapped command; and
- a sensory deprivation device controller for performing the mapped command and providing at least one of an audio and visual confirmation to a the user in the flotation space.

18. A sensory deprivation flotation system configured with an audio sensor disposed for detecting audio within a flotation space of the sensory deprivation system, comprising:
- an audio capture and processing system for differentiating audio captured by the audio sensor between sounds that are candidates for corresponding to one or more sensory deprivation flotation system control commands and other sounds, wherein differentiating is based on a set of sounds associated with a plurality of phases of a flotation session and a library of human utterances that correspond to the one or more sensory deprivation flotation system control commands; and
- a flotation system control system that controls aspects of the flotation system for sound candidates that correspond to the one or more sensory deprivation flotation system control commands.

19. The system of claim 18, wherein controlling aspects of the flotation system is based on the library of human utterances and a current phase of the flotation session.

* * * * *